US012649763B2

(12) United States Patent
Sporn

(10) Patent No.: US 12,649,763 B2
(45) Date of Patent: Jun. 9, 2026

(54) ANALOGS OF CDDO-2P-IM AND CDDO-3P-IM

(71) Applicant: TRITERPENOID THERAPEUTICS, INC., Lebanon, NH (US)

(72) Inventor: Michael B. Sporn, Tunbridge, VT (US)

(73) Assignee: TRITERPENOID THERAPEUTICS, INC., Lebanon, NH (US)

( * ) Notice: Subject to any disclaimer, the term of this patent is extended or adjusted under 35 U.S.C. 154(b) by 529 days.

(21) Appl. No.: 18/245,109

(22) PCT Filed: Sep. 14, 2021

(86) PCT No.: PCT/US2021/050183
§ 371 (c)(1),
(2) Date: Mar. 13, 2023

(87) PCT Pub. No.: WO2022/056439
PCT Pub. Date: Mar. 17, 2022

(65) Prior Publication Data

US 2023/0365621 A1 Nov. 16, 2023

Related U.S. Application Data

(60) Provisional application No. 63/077,873, filed on Sep. 14, 2020, provisional application No. 63/077,869, filed on Sep. 14, 2020.

(51) Int. Cl.
*C07J 63/00* (2006.01)
*A61P 35/00* (2006.01)

(52) U.S. Cl.
CPC ............. *C07J 63/008* (2013.01); *A61P 35/00* (2018.01)

(58) Field of Classification Search
CPC ...................................................... C07J 63/008
See application file for complete search history.

(56) References Cited

U.S. PATENT DOCUMENTS

| | | | |
|---|---|---|---|
| 2017/0267713 | A1 | 9/2017 | Gribble et al. |
| 2018/0127379 | A1 | 5/2018 | Sporn et al. |
| 2018/0161311 | A1 | 6/2018 | Sporn et al. |
| 2019/0135763 | A1 | 5/2019 | Gribble et al. |
| 2019/0381023 | A1 | 12/2019 | Kahrs |

FOREIGN PATENT DOCUMENTS

| | | |
|---|---|---|
| WO | WO 2008111497 | 9/2008 |
| WO | WO 2020068689 | 4/2020 |
| WO | 2020167969 A1 | 8/2020 |
| WO | 2022056439 A1 | 3/2022 |

OTHER PUBLICATIONS

Cao et al., "Novel synthetic pyridyl analogues of CDDO-Imidazolide are useful new tools in cancer prevention," Pharmacological Research. Jul. 31, 2015 (Jul. 31, 2015) vol. 100, p. 135-147.
International Search Report for International Patent Application No. PCT/US2021/050183, mailed Dec. 30, 2021, 3 pages.
Written Opinion for International Patent Application No. PCT/US2021/050183, mailed Dec. 30, 2021, 4 pages.
Yates, et al., "Pharmacodynamic characterization of chemopreventive triterpenoids as exceptionally potent inducers of Nrf2-regulated genes," Mol Cancer Ther, 6(1):154-162, 2007.

*Primary Examiner* — Susanna Moore
(74) *Attorney, Agent, or Firm* — Neal, Gerber & Eisenberg LLP

(57) ABSTRACT

The present disclosure relates to synthetic triterpenoids, methods for preparing such synthetic triterpenoids, and methods of using such synthetic triterpenoids to treat and/or prevent diseases or disorders such as cancers, particularly brain tumors, neuropsychiatric disorders, and neurodegenerative diseases.

22 Claims, No Drawings

ANALOGS OF CDDO-2P-IM AND CDDO-3P-IM

CROSS REFERENCE TO RELATED APPLICATIONS

This application is a national stage entry pursuant to 35 U.S.C. § 371 of International Application No. PCT/US2021/050183, which was filed on Sep. 14, 2021, which claims priority to U.S. Patent Application Nos. 63/077,869 and 63/077,873, which were filed on Sep. 14, 2020, the entire contents of which are incorporated herein by reference.

FIELD OF THE INVENTION

The present disclosure provides a new class of synthetic triterpenoids and their use to treat diseases or disorders such as cancers, particularly brain tumors, autoimmune diseases, inflammatory diseases, neuropsychiatric disorders, neurodegenerative diseases, and renal/kidney disease.

BACKGROUND OF THE INVENTION

Triterpenoids, biosynthesized in plants by the cyclization of squalene, are used for medicinal purposes in many Asian countries; and some, like ursolic and oleanolic acids, are known to be anti-inflammatory and anti-carcinogenic. However, the biological activity of these naturally occurring molecules is relatively weak, and therefore the synthesis of new analogs to enhance their potency has been undertaken.

In this respect, synthetic derivatives of oleanolic acid exhibit anti-inflammatory and anticancer activity. Such compounds include, for example, 2-cyano-3,12-dioxooleana-1,9(11)-dien-28-oic acid ("CDDO") and its C-28 methyl ester derivative 2-cyano-3,12-dioxoolean-1,9(11)-dien-28-oic acid methyl ester ("CDDO-Me") and its C-28 imidazole derivative 1-(2-cyano-3,12-dioxooleana-1,9(11)-dien-28-oyl) imidazole ("CDDO-Im"). See Honda et al., *Bioorg Med Chem Lett.* 8(19):2711-2714 (1998); Suh et al., *Cancer Res.* 58:717-723 (1998); Honda et al., *Bioorg Med Chem Lett.* 9(24):3429-3434 (1999); WO 1999/065478; WO 2004/064723. CDDO-Me is being developed for the treatment of kidney diseases, such as Alport syndrome and diabetic kidney disease. Furthermore, pyridyl analogs of CDDO-Im, such as 1-[2-Cyano-3,12-dioxooleana-1,9(11)-dien-28-oyl]-4(-pyridin-3-yl)-1H-imidazole ("CDDO-3P-Im"), have been synthesized and tested for activity in certain contexts. See Cao et al., *Pharmacol Res.* 100:135-47 (2015); WO 2016/033132.

Gliomas (Grade I-IV) are lethal primary brain tumors that make up eighty percent of all malignant brain tumors and about thirty percent of all central nervous system tumors. Low-grade gliomas (grade I & II) increase in time to become high grade gliomas (Grade III & IV). These recur in more than 90% of cases and have a median survival rate of 14 months and a 5-year survival rate of less than 10%. Glioblastoma multiforme (GBM) is the most common primary brain tumor. Survival rates in GBM are poor with less than 5% of patients surviving 5 years following diagnosis, with no notable improvement in population statistics in the last three decades, highlighting a desperate need for new and innovative approaches to treat this lethal disease.

For adult patients with newly diagnosed GBM, temozolomide (TMZ) is now given concomitantly with radiation therapy and then as maintenance treatment. Despite the addition of TMZ to the standard of care over a decade ago, the average length of survival for a patient with GBM remains at 14 months. Moreover, prolonged exposure to TMZ is associated with significant toxicity, including profound lymphopenia, and with the development of drug resistance. Because GBM is currently often incurable, there is a dire need for novel drugs that target mechanisms that underlie therapy resistance in GBM and that can enhance the response TMZ and radiation.

Neurodegenerative diseases are associated with the progressive loss of structure and/or function central nervous system (CNS) cells. Despite the enormous scientific effort devoted in the last two decades to developing pharmacological approaches for neurodegenerative diseases, very few effective drugs have been discovered. Thus, there are few effective therapies for most of these devastating disorders, such as Alzheimer's disease (AD), amyotrophic lateral sclerosis (ALS), and Parkinson's disease (PD).

The blood-brain barrier (BBB) is formed by specialized tight junctions between endothelial cells that line brain capillaries to create a highly selective barrier between the brain and the rest of the body. Overcoming the difficulty of delivering therapeutic agents to the specific CNS sites is one of the major challenges in discovery of new treatments of CNS diseases and disorders, such as brain tumors, neuropsychiatric diseases, and neurodegenerative diseases.

SUMMARY OF THE INVENTION

The present disclosure relates to novel compounds and, in particular, analogs of CDDO-2P-Im or CDDO-3P-Im having a lipophilicity-enhancing moiety. In certain embodiments, the lipophilicity-enhancing moiety replaces a hydrogen atom in the pyridyl ring of CDDO-2P-Im. In certain embodiments, the lipophilicity-enhancing moiety replaces a hydrogen atom in the pyridyl ring of CDDO-3P-Im.

In one aspect, the present disclosure relates to a compound of Formula (I), an N-oxide thereof, or a pharmaceutically acceptable salt thereof:

(I)

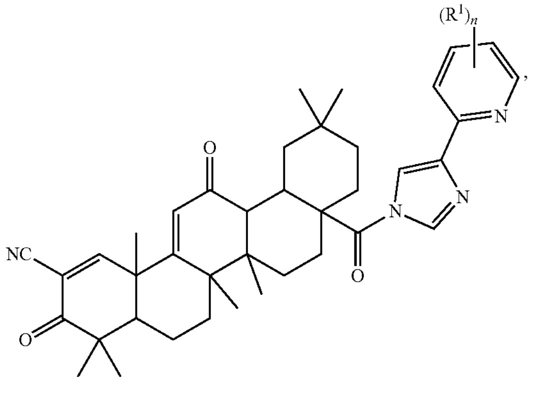

wherein n is an integer selected from 1 to 4. In certain embodiments, $R^1$ is a lipophilicity-enhancing moiety. In certain embodiments, $R^1$ is halogen, optionally substituted carboxamide, or optionally substituted $C_{1-6}$-haloalkyl, such as $C_{1-6}$-fluoroalkyl.

In certain embodiments, n is 1 and $R^1$ is $C_{1-6}$-fluoroalkyl, preferably —$CF_3$.

The present disclosure also relates to the use of such compounds, N-oxides, or salts as biologically active (e.g., therapeutic) components in, for example, pharmaceutical compositions and/or directly as human and/or animal therapeutics and medicines.

In one aspect, this disclosure provides a method for modulating Nrf2 activity. The method comprises administering a compound disclosed herein, an N-oxide thereof, or a pharmaceutically acceptable salt thereof to a patient in need thereof. In some embodiments, the compound is selected from the list of compounds in Tables A-B.

In another aspect, this disclosure provides a method for treating a disease or condition that is at least partially mediated by inflammasome activity, particularly NLRP3 inflammasome activity. The method comprises administering a compound disclosed herein, an N-oxide thereof, or a pharmaceutically acceptable salt thereof to a patient in need thereof. In some embodiments, the compound is selected from the list of compounds in Tables A-B.

In one aspect, the present disclosure relates to a compound of Formula (III), an N-oxide thereof, or a pharmaceutically acceptable salt thereof:

(III)

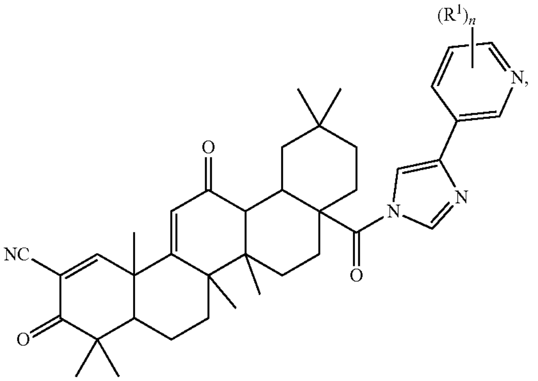

wherein n is an integer selected from 1 to 4. In certain embodiments, $R^1$ is a lipophilicity-enhancing moiety. In certain embodiments, $R^1$ is halogen, optionally substituted carboxamide, or optionally substituted $C_{1-6}$-haloalkyl, such as $C_{1-6}$-fluoroalkyl.

In certain embodiments, n is 1 and $R^1$ is $C_{1-6}$-fluoroalkyl, preferably —$CF_3$.

The present disclosure also relates to the use of such compounds, N-oxides, or salts as biologically active (e.g., therapeutic) components in, for example, pharmaceutical compositions and/or directly as human and/or animal therapeutics and medicines.

In one aspect, this disclosure provides a method for modulating Nrf2 activity. The method comprises administering a compound disclosed herein, an N-oxide thereof, or a pharmaceutically acceptable salt thereof to a patient in need thereof. In some embodiments, the compound is selected from the list of compounds in Tables C-D.

In another aspect, this disclosure provides a method for treating a disease or condition that is at least partially mediated by inflammasome activity, particularly NLRP3 inflammasome activity. The method comprises administering a compound disclosed herein, an N-oxide thereof, or a pharmaceutically acceptable salt thereof to a patient in need thereof. In some embodiments, the compound is selected from the list of compounds in Tables C-D.

The compounds, pharmaceutical compositions comprising the compounds, and methods for treating or preventing conditions, disorders, or diseases by administering the compounds are further described herein.

These and other objects of the invention are described in the following paragraphs. These objects should not be deemed to narrow the scope of the invention.

DESCRIPTION OF THE INVENTION

This detailed description is intended only to acquaint others skilled in the art with the present invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

In one aspect, the present disclosure relates to a compound of Formula (I), an N-oxide thereof, or a pharmaceutically acceptable salt thereof:

(I)

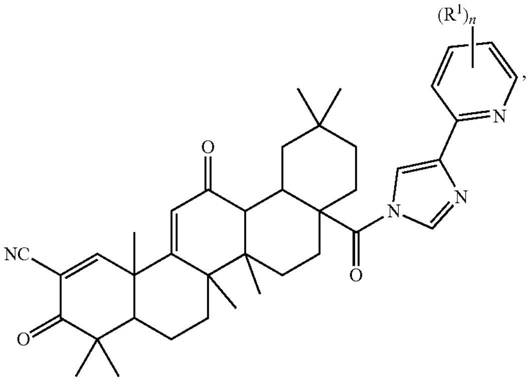

wherein n is an integer selected from 1 to 4. In certain embodiments, $R^1$ is a lipophilicity-enhancing moiety. In certain embodiments, $R^1$ is halogen, optionally substituted carboxamide, or optionally substituted $C_{1-6}$-haloalkyl, such as $C_{1-6}$-fluoroalkyl. In certain embodiments, n is 1 and $R^1$ is $C_{1-6}$-fluoroalkyl, preferably —$CF_3$. In certain embodiments, n is 1 and $R^1$ is an unsubstituted carboxamide (i.e., —C(O)$NH_2$).

In certain embodiments, the present disclosure relates to a compound of Formula (II), an N-oxide thereof, or a pharmaceutically acceptable salt thereof:

(II)

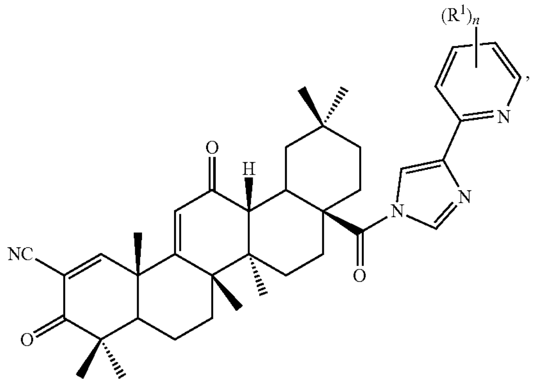

wherein n is an integer selected from 1 to 4. In certain embodiments, $R^1$ is a lipophilicity-enhancing moiety. In certain embodiments, $R^1$ is halogen, optionally substituted carboxamide, or optionally substituted $C_{1-6}$-haloalkyl, such as $C_{1-6}$-fluoroalkyl. In certain embodiments, n is 1 and $R^1$ is $C_{1-6}$-fluoroalkyl, preferably —$CF_3$. In certain embodiments, n is 1 and $R^1$ is an unsubstituted carboxamide (i.e., —$C(O)NH_2$).

In one aspect, the present disclosure relates to a compound of Formula (III), an N-oxide thereof, or a pharmaceutically acceptable salt thereof:

(III)

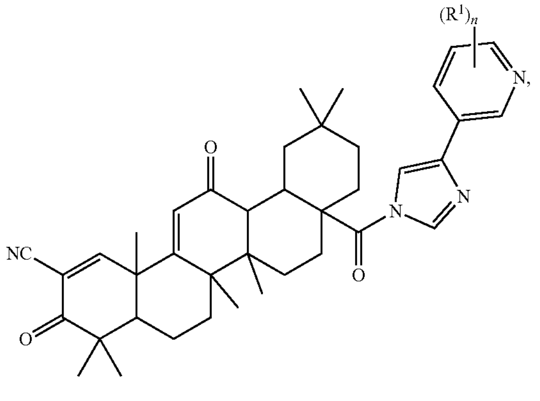

wherein n is an integer selected from 1 to 4. In certain embodiments, $R^1$ is a lipophilicity-enhancing moiety. In certain embodiments, $R^1$ is halogen, optionally substituted carboxamide, or optionally substituted $C_{1-6}$-haloalkyl, such as $C_{1-6}$-fluoroalkyl. In certain embodiments, n is 1 and $R^1$ is $C_{1-6}$-fluoroalkyl, preferably —$CF_3$. In certain embodiments, n is 1 and $R^1$ is an unsubstituted carboxamide (i.e., —$C(O)NH_2$).

In certain embodiments, the present disclosure relates to a compound of Formula (IV), an N-oxide thereof, or a pharmaceutically acceptable salt thereof:

(IV)

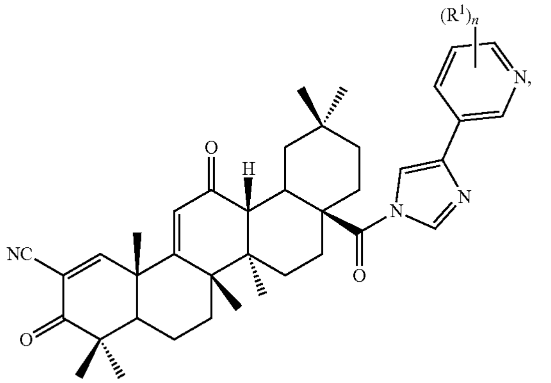

wherein n is an integer selected from 1 to 4. In certain embodiments, $R^1$ is a lipophilicity-enhancing moiety. In certain embodiments, $R^1$ is halogen, optionally substituted carboxamide, or optionally substituted $C_{1-6}$-haloalkyl, such as $C_{1-6}$-fluoroalkyl. In certain embodiments, n is 1 and $R^1$ is $C_{1-6}$-fluoroalkyl, preferably —$CF_3$. In certain embodiments, n is 1 and $R^1$ is an unsubstituted carboxamide (i.e., —$C(O)NH_2$).

The lipophilicity of a compound of the disclosure can be quantified by a c Log P (computed log octanol/water partition value) value. In some such embodiments, the c Log P value for a compound refers to the logarithm of its partition coefficient between n-octanol and water $\log(c_{octanol}/c_{water})$ as is known by those skilled in the art. High lipophilicity corresponds to a high c Log P value.

In certain embodiments, the lipophilicity-enhancing moiety increases c Log P and provides a BBB permeability function (i.e., enhancing passive transport through the BBB into the brain). In certain embodiments, a compound of the present disclosure can be configured with a combination of moieties and/or substituents to have specific c Log P values in a range of 0.5 to 4.5, preferably in the range of 1.0 to 3.0.

A. DEFINITIONS

As used in the specification and the appended claims, unless specified to the contrary, the following terms have the meaning indicated:

The term "about" as used herein means approximately, and in most cases within 10% of the stated value.

The term "alkyl" as used herein refers to unbranched (linear) or branched saturated hydrocarbon groups having the specified number of carbon atoms. $C_{1-6}$-alkyl, for example, includes a $C_1$ alkyl group up to and including $C_6$ alkyl groups. The alkyl group can be unsubstituted or substituted with one or more groups including, but not limited to, halo, aryl, heteroaryl, amino, carbonyl, and/or hydroxyl.

The term "brain tumor" includes a glioma, such as an astrocytoma (e.g., anaplastic astrocytoma), glioblastoma, ependymoma (e.g., anaplastic ependymoma or myxopapillary ependymoma), oligodendroglioma (e.g., anaplastic oligodendroglioma or anaplastic oligoastrocytoma), and all gliomas classified under WHO Grade 1 to Grade 4.

The term "carboxamide" as used herein refers to a —$C(O)NH_2$ group.

The term "halo" or "halogen" as used herein includes an atom selected from fluorine, chlorine, bromine, and iodine.

The term "haloalkyl" refers to an unbranched (linear) or branched alkyl group substituted with one or more halogen atoms, which may be the same or different and are selected from fluorine, chlorine, bromine, and iodine. Examples of haloalkyl include, but are not limited to, fluoromethyl, difluoromethyl, trifluoromethyl, trichloromethyl, 2,2,2-trifluoroethyl, 2,2,2-trichloroethyl, 2,2,3,3-tetrafluoropropyl, and 2,2,3,3,3-pentafluoropropyl.

The term "N-oxide" as used herein refers to compounds of the invention in which a nitrogen atom of a heterocyclic ring has been oxidized to the corresponding N-oxide and includes, but is not limited to, pyridyl N-oxide derivatives of the compounds of the invention. Such compounds may be prepared by oxidation of the pyridyl nitrogen atom by a suitable oxidizing agent. N-oxidized derivatives may be identified, for example, by detection of a molecule or adduct having an additional 16 Mass Units on a chromatogram resulting from the addition of an oxygen atom (mass 16) to the pyridyl nitrogen atom.

The term "pharmaceutically acceptable" is used adjectivally to mean that the modified noun is appropriate for use as a pharmaceutical product for human use or as a part of a pharmaceutical product for human use.

The term "pharmacokinetic parameter(s)" refers to any suitable pharmacokinetic parameter, such as $T_{max}$, $C_{max}$, and AUC. The term "$C_{max}$" refers to the peak concentration and, in particular, the maximum observed plasma/serum concentration of drug. The term "$T_{max}$" refers to the time to reach the peak concentration. The term "$AUC_t$" refers to the area under the plasma concentration-time curve, where t is the time of the last measurable plasma concentration in the study. The term "$AUC_\infty$" refers to the area under the plasma concentration-time curve from time zero to infinity following a single dose.

B. COMPOUNDS

In one aspect, compounds disclosed herein possess biological activity, for example, by acting on one or more endogenous pathways, such as the Kelch-Like ECH-Associated Protein 1 (Keap1)-nuclear factor erythroid-2 (NF-E2)-related factor 2 (NRF2) pathway and/or pathways regulating NLRP3 inflammasome activity. In certain embodiments, a compound disclosed herein may be transformed in vivo into a metabolite, which itself biological activity and/or can be further transformed into a molecule possessing biological activity.

In one aspect, this disclosure provides a compound of Formula (II), an N-oxide thereof, or a pharmaceutically acceptable salt thereof:

(II)

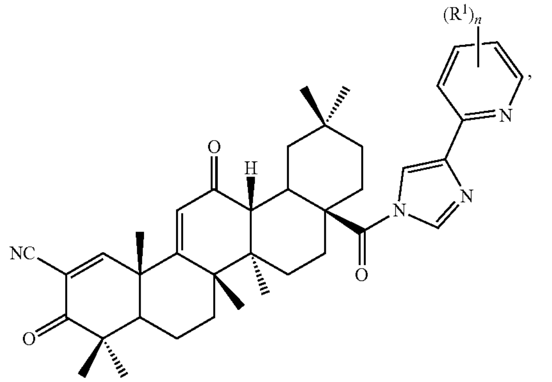

wherein n is an integer selected from 1 to 4 and $R^1$ is halogen, optionally substituted carboxamide, or optionally substituted $C_{1-6}$-haloalkyl, such as $C_{1-6}$-fluoroalkyl.

In certain embodiments, n is 1. In certain embodiments, n is 2. In certain embodiments, n is 3. In certain embodiments, n is 4.

In certain embodiments, $R^1$ is halogen, preferably fluoro or chloro.

In certain embodiments, $R^1$ is $C_{1-6}$-haloalkyl, preferably $C_{1-3}$-haloalkyl. In some such embodiments, $R^1$ is fluoromethyl, difluoromethyl, trifluoromethyl, trichloromethyl, 2,2,2-trifluoroethyl, 2,2,2-trichloroethyl, 2,2,3,3-tetrafluoropropyl, 2,2,3,3,3-pentafluoropropyl. In some such embodiments, $R^1$ is $-CF_3$, $-CHF_2$, $-CH_2F$, $-CH_2CF_3$, $-CH_2CHF_2$, $-CH_2CH_2F$, $-CF_2CF_3$, $-CHFCF_3$, $-CHFCH_2F$, $-CF_2CH_2F$, or $-CF_2CHF_2$.

In certain embodiments, $R^1$ is an unsubstituted carboxamide (i.e., $-C(O)NH_2$). In certain embodiments, $R^1$ is a substituted carboxamide. In some such embodiments, the substituted carboxamide is a carboxamide moiety having at least one hydrogen atom replaced with an alkyl, alkenyl, alkynyl, aryl, or heteroaryl.

In certain embodiments, the compound has a structure corresponding to Formula (II-A), Formula (II-B), Formula (II-C), or Formula (II-D):

(IIA)

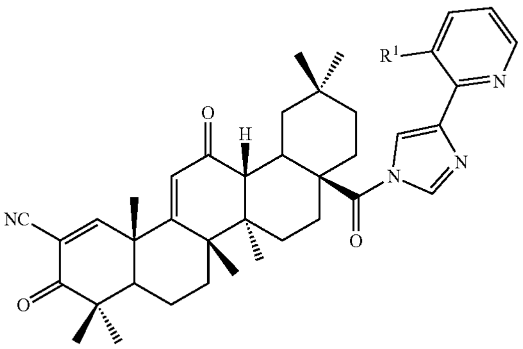

(IIB)

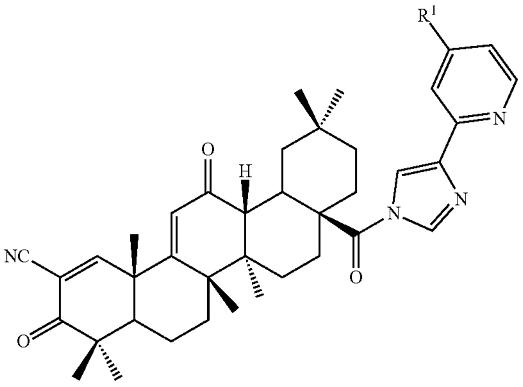

-continued (IIC)

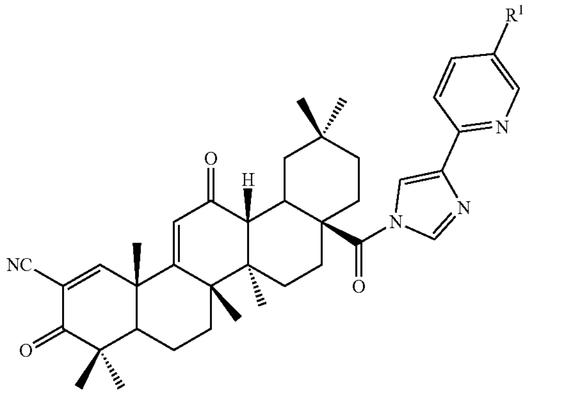

-continued (IID)

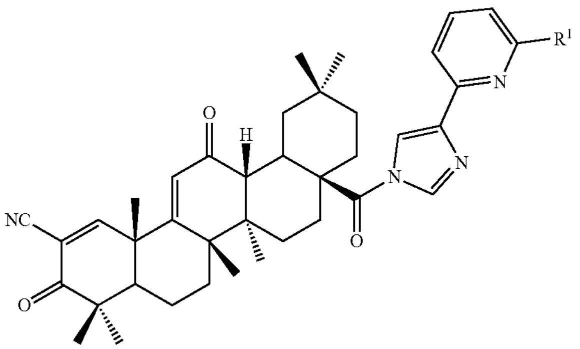

In one aspect, this disclosure provides a compound, an N-oxide thereof, or salt thereof, wherein the compound has a structure corresponding to one of the examples listed in Table A.

Select compounds are shown in Table A:

| Ex. | Structure | Trivial Name |
|---|---|---|
| 101 | 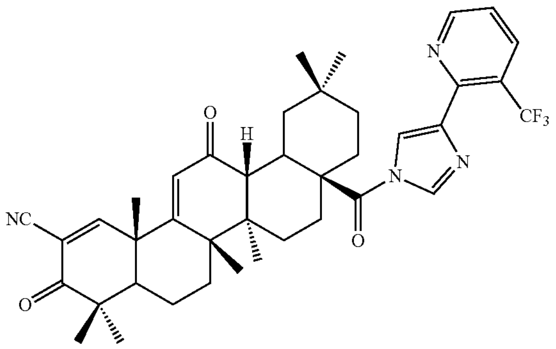<br>(6aS,6bR,8aS,12bR,14bS)-4,4,6a,6b,11,11,14b-heptamethyl-3,13-dioxo-8a-(4-(3-(trifluoromethyl)pyridin-2-yl)-1H-imidazole-1-carbonyl)-3,4,4a,5,6,6a,6b,7,8,8a,9,10,11,12,12a,12b,13,14b-octadecahydropicene-2-carbonitrile | CDDO-2P-Im-3-CF3 |
| 102 | 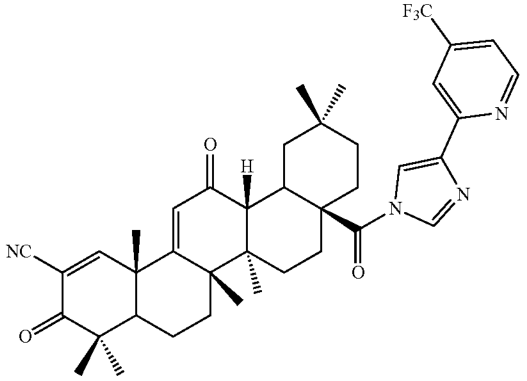<br>(6aS,6bR,8aS,12bR,14bS)-4,4,6a,6b,11,11,14b-heptamethyl-3,13-dioxo-8a-(4-(4-(trifluoromethyl)pyridin-2-yl)-1H-imidazole-1-carbonyl)-3,4,4a,5,6,6a,6b,7,8,8a,9,10,11,12,12a,12b,13,14b-octadecahydropicene-2-carbonitrile | CDDO-2P-Im-4-CF3 |

-continued

| Ex. | Structure | Trivial Name |
|---|---|---|
| 103 | 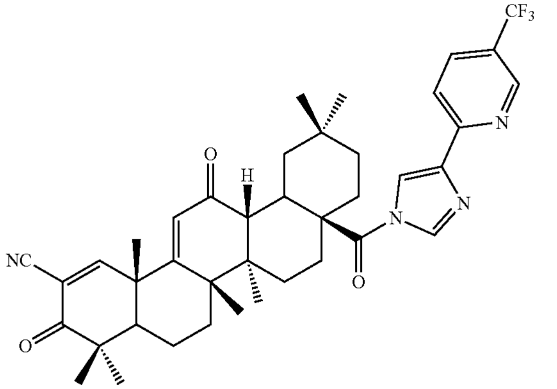 (6aS,6bR,8aS,12bR,14bS)-4,4,6a,6b,11,11,14b-heptamethyl-3,13-dioxo-8a-(4-(5-(trifluoromethyl)pyridin-2-yl)-1H-imidazole-1-carbonyl)-3,4,4a,5,6,6a,6b,7,8,8a,9,10,11,12,12a,12b,13,14b-octadecahydropicene-2-carbonitrile | CDDO-2P-Im-5-CF3 |
| 104 | 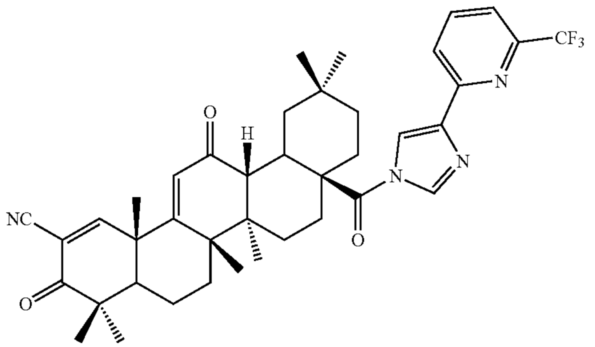 (6aS,6bR,8aS,12bR,14bS)-4,4,6a,6b,11,11,14b-heptamethyl-3,13-dioxo-8a-(4-(6-(trifluoromethyl)pyridin-2-yl)-1H-imidazole-1-carbonyl)-3,4,4a,5,6,6a,6b,7,8,8a,9,10,11,12,12a,12b,13,14b-octadecahydropicene-2-carbonitrile | CDDO-2P-Im-6-CF3 |

In one aspect, this disclosure provides a compound, an N-oxide thereof, or salt thereof, wherein the compound has a structure corresponding to one of the examples listed in Table B.

Select compounds are shown in Table B:

| Ex. | Structure | Trivial Name |
|---|---|---|
| 201 | 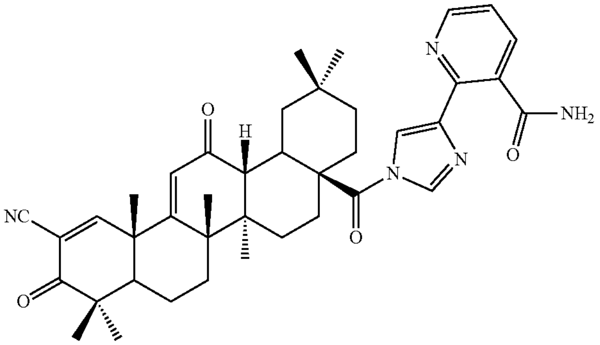 2-(1-((4aS,6aR,6bS,12aS,14aR)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicene-4a-carbonyl)-1H-imidazol-4-yl)nicotinamide | CDDO-2P-Im-3-Carboxamide |

-continued

| Ex. | Structure | Trivial Name |
|---|---|---|
| 202 | 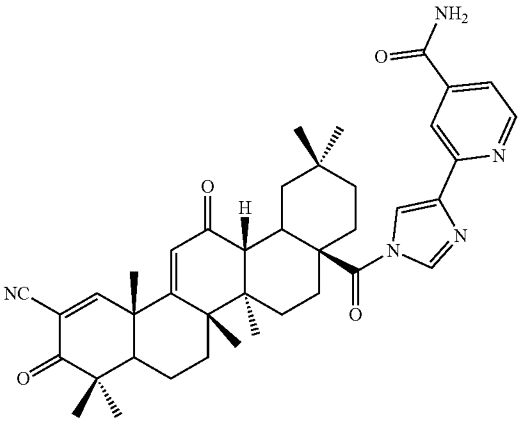 2-(1-((4aS,6aR,6bS,12aS,14aR)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicene-4a-carbonyl)-1H-imidazol-4-yl)isonicotinamide | CDDO-2P-Im-4-Carboxamide |
| 203 | 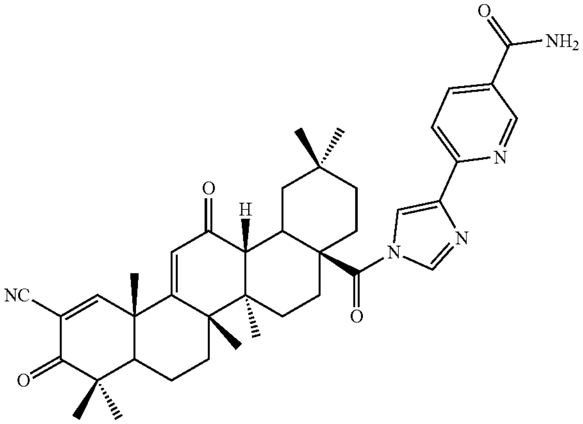 6-(1-((4aS,6aR,6bS,12aS,14aR)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicene-4a-carbonyl)-1H-imidazol-4-yl)nicotinamide | CDDO-2P-Im-5-Carboxamide |
| 204 | 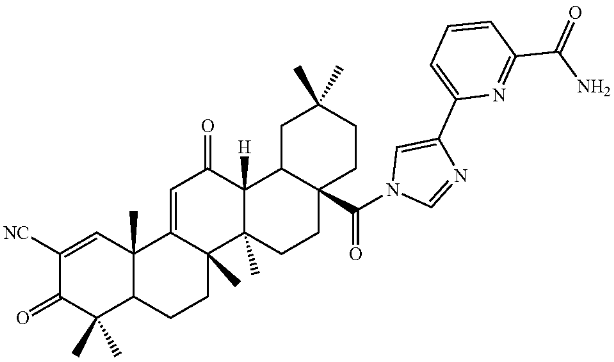 6-(1-((4aS,6aR,6bS,12aS,14aR)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicene-4a-carbonyl)-1H-imidazol-4-yl)picolinamide | CDDO-2P-Im-6-Carboxamide |

In one aspect, this disclosure provides a compound of Formula (IV), an N-oxide thereof, or a pharmaceutically acceptable salt thereof:

(IV)

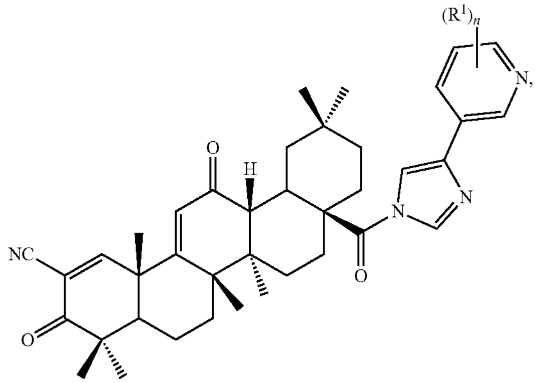

wherein n is an integer selected from 1 to 4 and $R^1$ is halogen, optionally substituted carboxamide, or optionally substituted $C_{1-6}$-haloalkyl, such as $C_{1-6}$-fluoroalkyl.

In certain embodiments, n is 1. In certain embodiments, n is 2. In certain embodiments, n is 3. In certain embodiments, n is 4.

In certain embodiments, $R^1$ is halogen, preferably fluoro or chloro.

In certain embodiments, $R^1$ is $C_{1-6}$-haloalkyl, preferably $C_{1-3}$-haloalkyl. In some such embodiments, $R^1$ is fluoromethyl, difluoromethyl, trifluoromethyl, trichloromethyl, 2,2,2-trifluoroethyl, 2,2,2-trichloroethyl, 2,2,3,3-tetrafluoropropyl, 2,2,3,3,3-pentafluoropropyl. In some such embodiments, $R^1$ is $—CF_3$, $—CHF_2$, $—CH_2F$, $—CH_2CF_3$, $—CH_2CHF_2$, $—CH_2CH_2F$, $—CF_2CF_3$, $—CHFCF_3$, $CHFCH_2F$, $—CF_2CH_2F$, or $—CF_2CHF_2$.

In certain embodiments, $R^1$ is an unsubstituted carboxamide (i.e., $—C(O)NH_2$). In certain embodiments, $R^1$ is a substituted carboxamide. In some such embodiments, the substituted carboxamide is a carboxamide moiety having at least one hydrogen atom replaced with an alkyl, alkenyl, alkynyl, aryl, or heteroaryl.

In certain embodiments, the compound has a structure corresponding to Formula (IV-A), Formula (IV-B), Formula (IV-C), or Formula (IV-D):

(IVA)

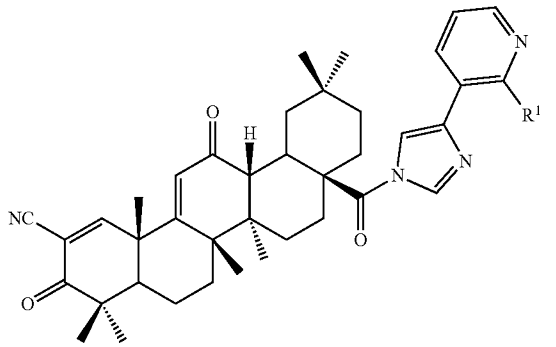

-continued (IVB)

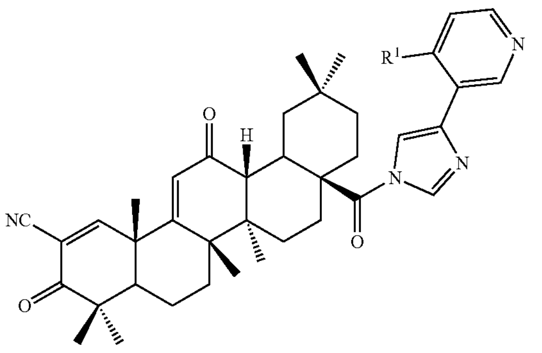

(IVC)

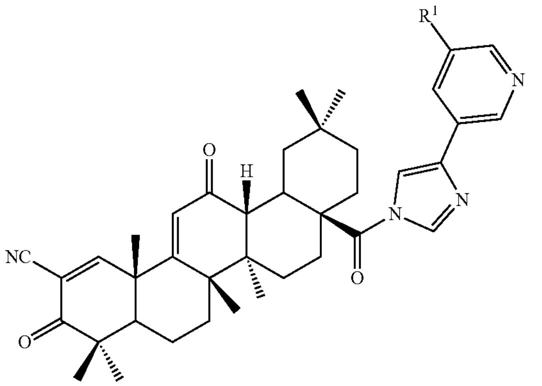

(IVD)

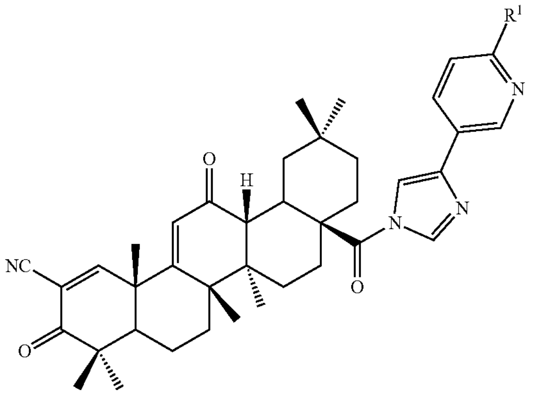

In one aspect, this disclosure provides a compound, an N-oxide thereof, or salt thereof, wherein the compound has a structure corresponding to one of the examples listed in Table C.

Select compounds are shown in Table C:

| Ex. | Structure | Trivial Name |
| --- | --- | --- |
| 301 | 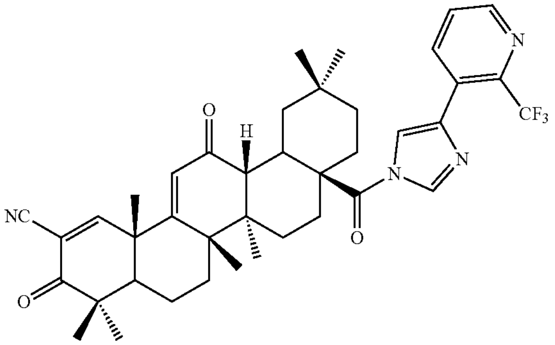 (6aS,6bR,8aS,12bR,14bS)-4,4,6a,6b,11,11,14b-heptamethyl-3,13-dioxo-8a-(4-(2-(trifluoromethyl)pyridin-3-yl)-1H-imidazole-1-carbonyl)-3,4,4a,5,6,6a,6b,7,8,8a,9,10,11,12,12a,12b,13,14b-octadecahydropicene-2-carbonitrile | CDDO-3P-Im-2-CF3 |
| 302 | 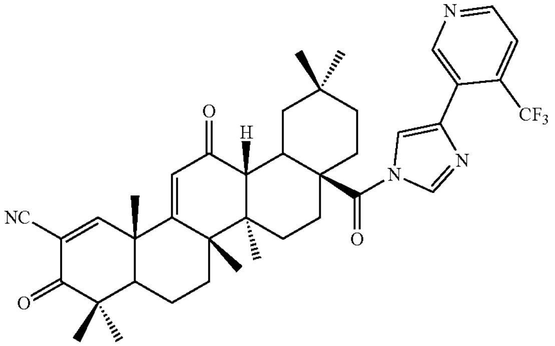 (6aS,6bR,8aS,12bR,14bS)-4,4,6a,6b,11,11,14b-heptamethyl-3,13-dioxo-8a-(4-(4-(trifluoromethyl)pyridin-3-yl)-1H-imidazole-1-carbonyl)-3,4,4a,5,6,6a,6b,7,8,8a,9,10,11,12,12a,12b,13,14b-octadecahydropicene-2-carbonitrile | CDDO-3P-Im-4-CF3 |
| 303 | 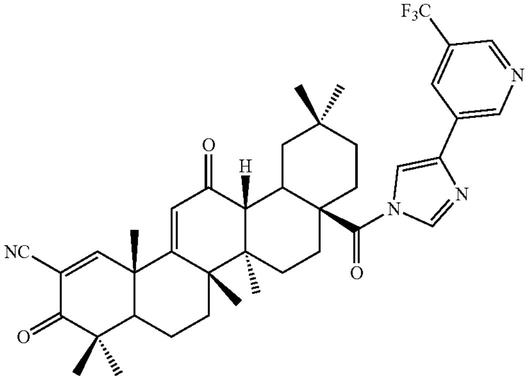 (6aS,6bR,8aS,12bR,14bS)-4,4,6a,6b,11,11,14b-heptamethyl-3,13-dioxo-8a-(4-(5-(trifluoromethyl)pyridin-3-yl)-1H-imidazole-1-carbonyl)-3,4,4a,5,6,6a,6b,7,8,8a,9,10,11,12,12a,12b,13,14b-octadecahydropicene-2-carbonitrile | CDDO-3P-Im-5-CF3 |

-continued

| Ex. | Structure | Trivial Name |
|---|---|---|
| 304 | 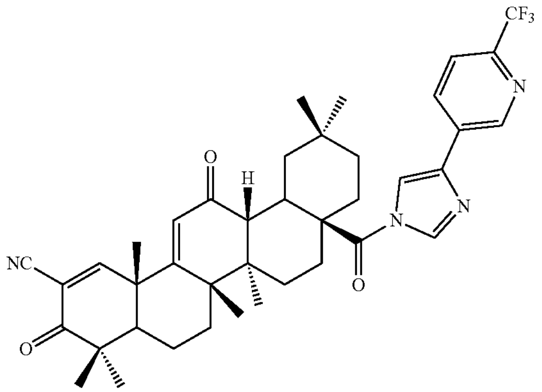<br>(6aS,6bR,8aS,12bR,14bS)-4,4,6a,6b,11,11,14b-heptamethyl-3,13-dioxo-8a-(4-(6-(trifluoromethyl)pyridin-3-yl)-1H-imidazole-1-carbonyl)-3,4,4a,5,6,6a,6b,7,8,8a,9,10,11,12,12a,12b,13,14b-octadecahydropicene-2-carbonitrile | CDDO-3P-Im-6-CF3 |

In one aspect, this disclosure provides a compound, an N-oxide thereof, or salt thereof, wherein the compound has a structure corresponding to one of the examples listed in Table D.

Select compounds are shown in Table D:

| Ex. | Structure | Trivial Name |
|---|---|---|
| 401 | 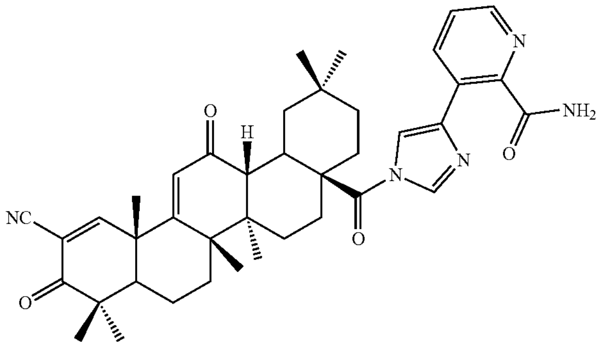 | CDDO-3P-Im-2-carboxamide |
| 402 | 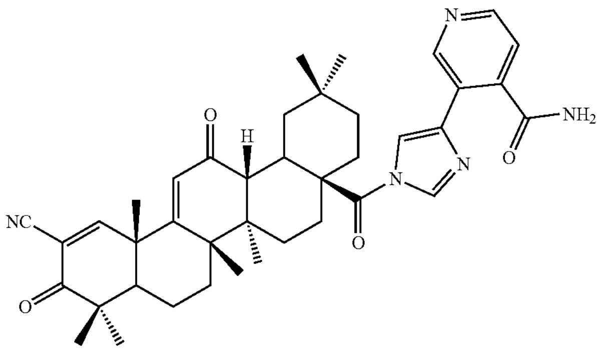 | CDDO-3P-Im-4-carboxamide |

-continued
| Ex. | Structure | Trivial Name |
| --- | --- | --- |
| 403 | 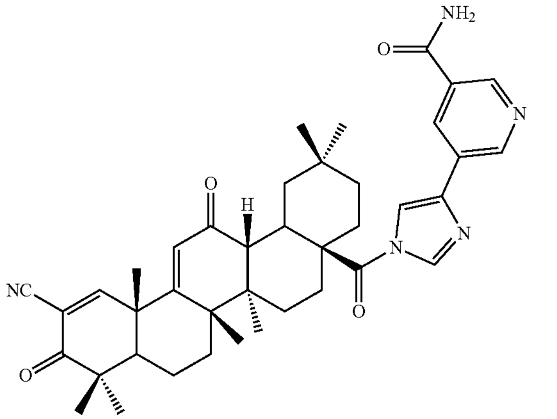 | CDDO-3P-Im-5-carboxamide |
| 404 | 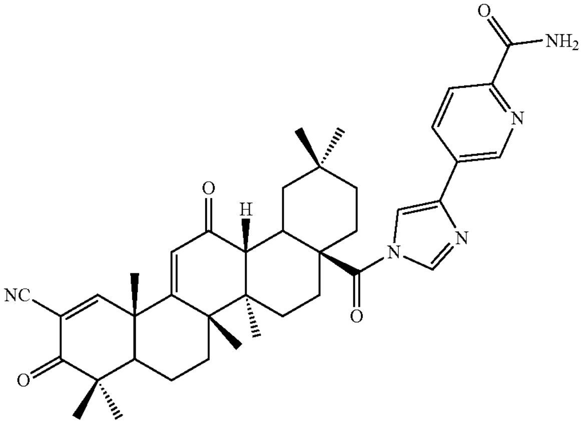 | CDDO-3P-Im-6-carboxamide |

C. SYNTHETIC METHODS

The following general scheme is representative of a particular embodiment of the method and allows for synthesis of certain compounds described herein:

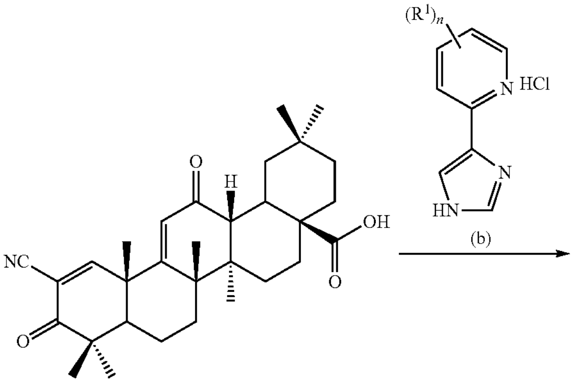
(b)

(a)

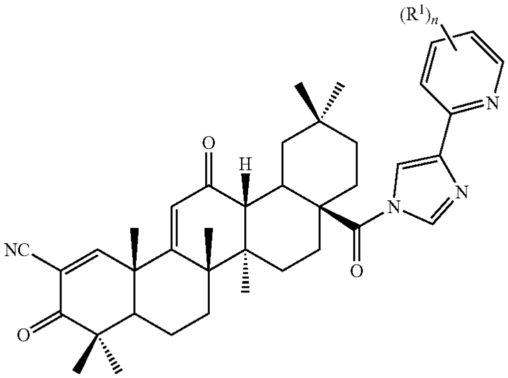

(II)

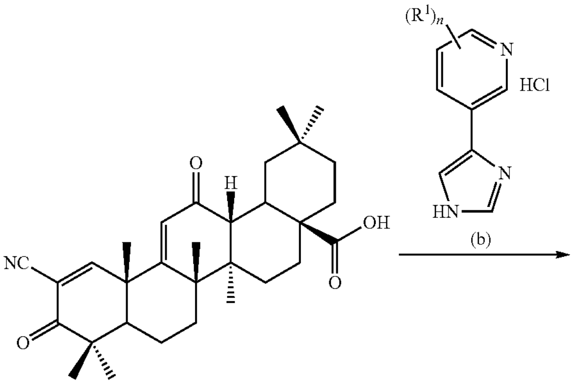
(b)

(a)

-continued

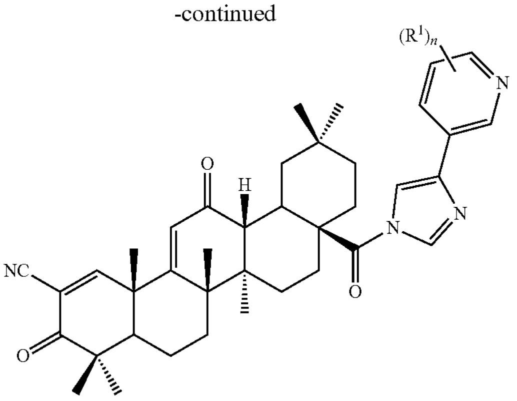

(IV)

As shown, the preparation of compounds disclosed herein can be achieved by coupling of a substituted imidazole (b) with CDDO (a), which is commercially available.

In certain embodiments, the substituted imidazole (b) can be prepared by substitution of an aryl bromide (e.g., a bromo-trifluoromethyl pyridine or a bromo-cyanopyridine) in the presence of a catalyst, such as tetrakis(triphenylphosphine)palladium. Thus, preparation of the substituted imidazole may involve a palladium-catalyzed coupling reaction, such as Stille coupling. The preparation of the substituted imidazole may further involve deprotection, such as trityl deprotection, according to methods known to those skilled in the art.

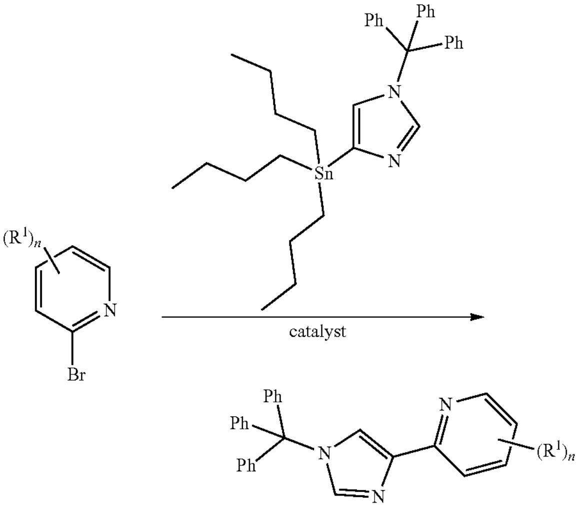

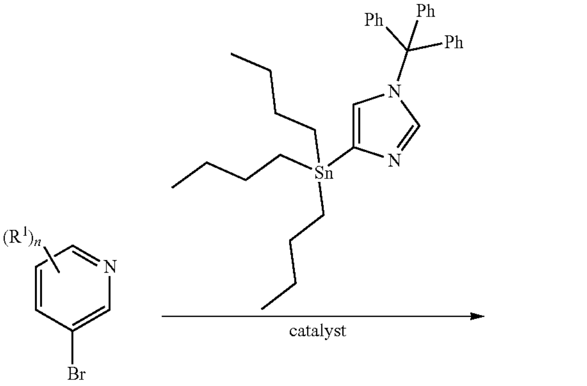

-continued

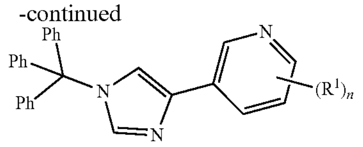

In the case of pyridyl carboxamide analogs, a hydrolysis step can be performed to convert, for example, a nitrile intermediate to a primary amide, as depicted below.

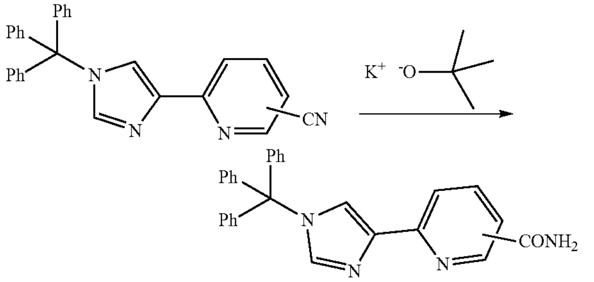

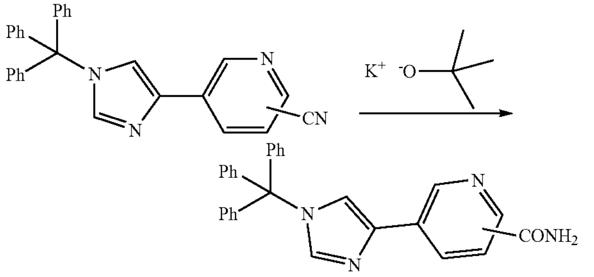

D. METHODS OF USE

In one aspect, this disclosure provides a method for treating or preventing a proliferative disease or disorder, such as cancer. The method comprises administering to a patient in need thereof a therapeutically effective amount of a compound described herein, an N-oxide thereof, or a pharmaceutically acceptable salt thereof. In some embodiments, the compound is a compound listed in Table A or Table B. In some embodiments, the compound is a compound listed in Table C or Table D. In some embodiments, the compound (or N-oxide thereof or pharmaceutically acceptable salt thereof) is administered orally. In certain embodiments, the cancer involves a solid tumor, such as a brain tumor (e.g., medulloblastoma or glioblastoma). In some such embodiments, the patient is an adult patient. In other such embodiments, the patient is a pediatric patient; for example, the pediatric patient may have a brain tumor, such as glioblastoma or medulloblastoma. In certain embodiments, the cancer is a blood cancer, such as leukemia, lymphoma, or myeloma; in some such embodiments the blood cancer is, for example, Hodgkin or non-Hodgkin lymphoma (e.g., diffuse large B cell lymphoma or mantle cell lymphoma).

In another aspect, this disclosure provides a method for treating a neurodegenerative disease. The method comprises administering to a patient in need thereof a therapeutically effective amount of a compound described herein, an N-oxide thereof, or a pharmaceutically acceptable salt thereof. In some embodiments, the compound is a compound listed in Table A or Table B. In some embodiments, the compound is a compound listed in Table C or Table D. In some embodiments, the compound (or N-oxide thereof or pharmaceutically acceptable salt thereof) is administered orally. In certain embodiments, the neurodegenerative disease is Alzheimer's disease (AD), Parkinson's disease (PD), amyotrophic lateral sclerosis (ALS), multiple sclerosis (MS), or Huntington disease.

In another aspect, this disclosure provides a method for treating an inflammatory disease or condition. The method comprises administering to a patient in need thereof a therapeutically effective amount of a compound described herein, an N-oxide thereof, or a pharmaceutically acceptable salt thereof. In some embodiments, the compound is a compound listed in Table A or Table B. In some embodiments, the compound is a compound listed in Table C or Table D. In some embodiments, the compound (or N-oxide thereof or pharmaceutically acceptable salt thereof) is administered orally. In certain embodiments, the inflammatory disease or condition is Crohn's disease, inflammatory bowel disease, rheumatoid arthritis, or another disease associated with aberrant inflammatory responses, which may include neuropsychiatric disorders and, particularly, depression. Thus, in certain embodiments, this disclosure provides a method for treating a neuropsychiatric disorder such as depression.

In yet another aspect, this disclosure provides a method for treating diseases of the lung (e.g., Chronic Obstructive Pulmonary Disease (COPD), emphysema, pulmonary fibrosis, bronchopulmonary dysplasia); diseases of the liver (e.g., chronic metabolic disease, liver injury from various toxins); diseases of the kidney (e.g., Alport syndrome and chronic kidney disease (CKD), including CKD resulting from diabetes, acute renal injury, and aging); and atherosclerosis. The method comprises administering to a patient in need thereof a therapeutically effective amount of a compound described herein, an N-oxide thereof, or a pharmaceutically acceptable salt thereof. In some embodiments, the compound is a compound listed in Table A or Table B. In some embodiments, the compound is a compound listed in Table C or Table D. In some embodiments, the compound (or N-oxide thereof or pharmaceutically acceptable salt thereof) is administered orally.

In another aspect, this disclosure provides a method for treating a host infected with a virus by administering a compound disclosed herein or an N-oxide thereof or a pharmaceutically acceptable salt thereof to the host. In certain embodiments, the host is a human. In certain embodiments, the virus belongs to the family Coronaviridae, Filoviridae, or Orthocoronavirinae. In some such embodiments, the virus is Influenza A. In some such embodiments, the virus is SARS-CoV-2. In some such embodiments, the host is in the early stages of a disease caused by the virus. When used to treat a viral infection, the compound (or N-oxide or salt) can be used in combination with one or more additional therapeutic or prophylactic agents, such as one more anti-viral agents. In some embodiments, the compound is a compound listed in Table A or Table B. In some embodiments, the compound is a compound listed in Table C or Table D. In some embodiments, the compound (or N-oxide thereof or pharmaceutically acceptable salt thereof) is administered orally.

In another aspect, this disclosure provides a method for treating a patient diagnosed with, or suspected of suffering from, a disease caused by a virus, such as COVID-19. The method includes administering a therapeutically effective amount a compound disclosed herein or an N-oxide thereof or a pharmaceutically acceptable salt thereof to the patient.

In certain embodiments, the patient is a human. In some such embodiments, the patient is confirmed to be positive for SARS-CoV-2. In other such embodiments, the patient is suspected to be positive for SARS-CoV-2. In some embodiments, the compound is a compound listed in Table A or Table B. In some embodiments, the compound is a compound listed in Table C or Table D. In some embodiments, the compound (or N-oxide thereof or pharmaceutically acceptable salt thereof) is administered orally.

In certain embodiments, for any of the aforementioned aspects, the patient is a mammal. In some such embodiments, the mammal is a human.

In certain embodiments, for any of the aforementioned aspects, the methods comprise administering to the subject a therapeutically effective amount of a compound described herein, an N-oxide thereof, or a pharmaceutically acceptable salt thereof as single agent or in combination with another therapeutic agent. In certain embodiments, the compound, N-oxide, or salt is co-administered or co-formulated with an oral chemotherapeutic agent. In some such embodiments, the oral chemotherapeutic agent is an alkylating agent. In some such embodiments, the alkylating agent is temozolomide, which is chemically described as 3,4-dihydro-3-methyl-4-oxoimidazo[5,1-d]as-tetrazine-8-carboxamide, available commercially as Temodar®, and approved to be used in the treatment of adult patients with (1) newly diagnosed glioblastoma multiforme concomitantly with radiotherapy and then as maintenance treatment and (2) refractory anaplastic astrocytoma patients who have experienced disease progression on a drug regimen containing nitrosourea and procarbazine. In certain embodiments, the compound, N-oxide, or salt is administered orally.

The preferred total daily dose of the compound, N-oxide, or salt (administered in single or divided doses) is typically from about 0.001 to about 100 mg/kg, more preferably from about 0.001 to about 30 mg/kg, and even more preferably from about 0.01 to about 10 mg/kg (i.e., mg of the compound, N-oxide, or salt per kg body weight). In certain embodiments, dosage unit compositions contain such amounts or submultiples thereof to make up the daily dose. In many instances, the administration of the compound, N-oxide, or salt will be repeated a plurality of times. In certain embodiments, multiple doses per day typically may be used to increase the total daily dose, if desired.

Factors affecting the preferred dosage regimen include the type, age, weight, sex, diet, and condition of the patient; the severity of the pathological condition; the route of administration; pharmacological considerations, such as the activity, efficacy, pharmacokinetic, and toxicology profiles of the particular compound or salt used; whether a drug delivery system is utilized; and whether the compound or salt is administered as part of a drug combination. Thus, the dosage regimen actually employed can vary widely, and therefore, can derive from the preferred dosage regimen set forth above.

The bioavailability and/or biological activity of a compound and/or its metabolite can be determined using various known methods. Measures of bioavailability include, but are not limited to, pharmacokinetic parameters, such as $T_{max}$, $C_{max}$, and AUC.

E. COMPOSITIONS

In at least one aspect, the present disclosure includes compositions comprising a compound described herein, an N-oxide thereof, or a pharmaceutically acceptable salt thereof. In certain embodiments, the composition comprises one or more conventional pharmaceutically acceptable excipients.

In some embodiments of any aspects disclosed herein, the compound may be present in a pharmaceutical composition in the form of acid or base addition salts. Acid addition salts may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Suitable base addition salts include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" is intended to encompass any and all acceptable salt forms.

Pharmaceutical compositions disclosed herein comprise a compound disclosed herein, an N-oxide thereof, or a pharmaceutically acceptable salt thereof. In some embodiments, the pharmaceutical composition is an oral dosage form, such as a tablet or capsule. In some such embodiments, the oral dosage form may comprise pharmaceutically acceptable excipients such as excipients that function as binders, glidants, lubricants, and fillers. Thus, an oral dosage form comprising a compound disclosed herein or a pharmaceutically acceptable salt thereof further optionally comprises one or more conventional pharmaceutically acceptable excipients.

In some embodiments, a compound is co-administered with at least one additional therapeutic agent. In some such embodiments, the additional therapeutic agent is temozolomide.

In some embodiments, the additional therapeutic agent and the compound of the present disclosure are co-administered to the patient in a substantially simultaneous manner (e.g., or within about 5 min of each other), in a sequential manner, or both. It is contemplated, for example, that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient. In some embodiments, the additional therapeutic agent and the compound of the present disclosure are administered in separate pharmaceutical compositions. In some embodiments, the additional therapeutic agent and the compound of the present disclosure are administered in the same pharmaceutical composition.

In at least one aspect, the present disclosure includes a pharmaceutical composition for use in modulating Nrf2 activity and/or treating a disease or condition that is at least partially mediated by inflammasome activity, particularly NLRP3 inflammasome activity. In certain embodiments, the composition comprises a compound disclosed herein, an N-oxide thereof, or a pharmaceutically acceptable salt thereof and a pharmaceutically acceptable excipient.

Tablets, capsules, or other dosages forms may be provided in discrete units conveniently contain a daily dose, or an appropriate fraction thereof, of the compound, N-oxide, or salt. The dosage form can contain a dose of about 0.5 mg to about 1500 mg, about 1 mg to about 300 mg, about 2.5 mg to about 100 mg, about 5 mg to about 30 mg, or increments therein of a compound described herein, an N-oxide thereof, or a pharmaceutically acceptable salt thereof.

It will be readily apparent to those skilled in the art that other suitable modifications and adaptations of the compositions and methods of the invention described herein may be made using suitable equivalents without departing from the scope of the invention or the embodiments disclosed herein.

F. EXAMPLES

Example 1

A. Preparation of (6aS,6bR,8aS,12bR,14bS)-4,4,6a,6b,11,11,14b-heptamethyl-3,13-dioxo-8a-(4-(6-(trifluoromethyl) pyridin-2-yl)-1H-imidazole-1-carbonyl)-3,4,4a,5,6,6a,6b,7,8,8a,9,10,11,12,12a,12b,13,14b-octadecahydropicene-2-carbonitrile (Compound 104)

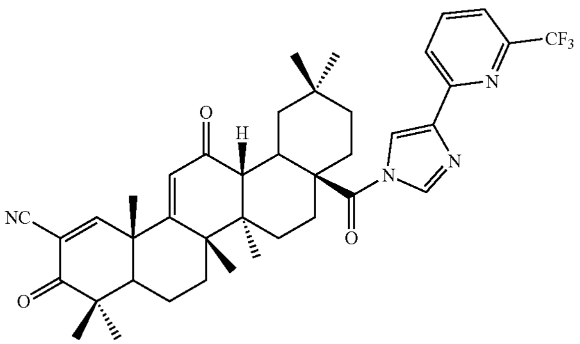

Stille Coupling

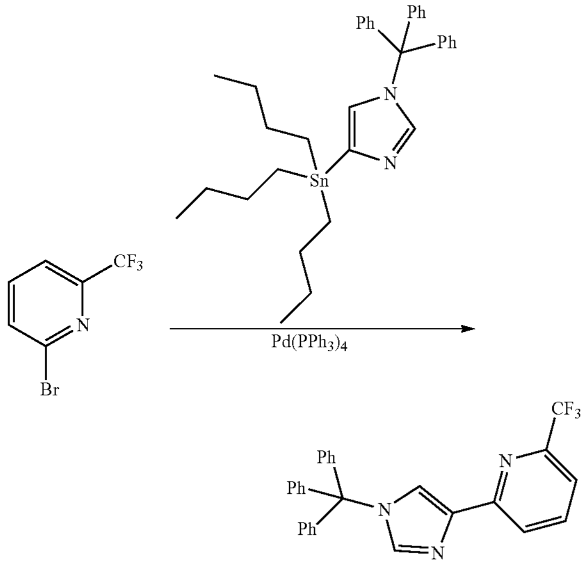

4-(Tributylstannyl)-trityl-1H-imidazole was prepared according to methods known in the art. See Jetter et al., Synthesis 6:829 (1998).

To a stirred solution of 4-(Tributylstannyl)-trityl-1H-imidazole (4.29 g. 7.15 mmol) in toluene (20 mL) was charged 2-bromo-6-(trifluoromethyl)pyridine (1.6 g, 7.08 mmol) and the mixture degassed with nitrogen for 15 minutes. Tetrakis (triphenylphosphine)palladium (0.245 g, 0.212 mmol) was added and the mixture heated to 100° C. and stirred for 18 h. The reaction mixture was cooled to 25° C. and 10% aqueous potassium fluoride (16 mL) solution was added and stirred for 30 minutes. The mixture was filtered through celite and the phases separated. The organic layer was washed twice with water (16 mL) and dried over anhydrous magnesium sulfate and concentrated. Purification by column chromatography (heptane/Ethyl acetate 4:1) gave the desired product as a yellow foam in 80% yield.

Trityl Deprotection

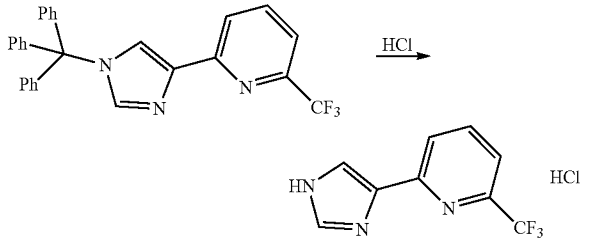

2-(trifluoromethyl)-6-(1-trityl-1H-imidazol-4-yl)pyridine (3.22 g, 7.07 mmol) was dissolved in dioxane (65 mL) and heated to 100° C. HCl in dioxane (5.3 mL, 21.2 mmol, 4M) was added and the mixture heated for 1 h. The mixture was cooled to RT, filtered and washed with dioxane (2×10 mL) and dried under vacuum to give the desired product as a white solid in 90% yield.

Coupling With CDDO

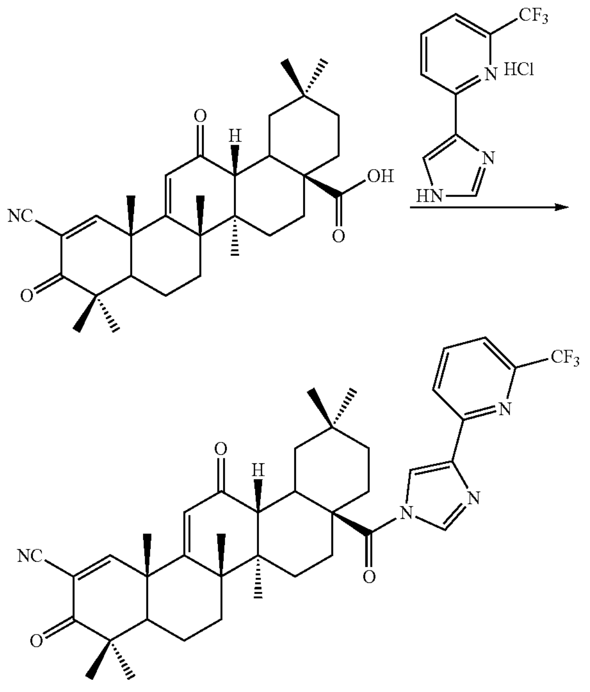

CDDO was obtained from a commercial supplier. To a stirred solution of CDDO (1 g, 2.03 mmol) in dichloromethane (10 mL) was added DMF (8 μL, 0.1 mmoL). Oxalyl chloride (0.25 mL, 2.85 mmol) was added over 15 min and the mixture stirred at RT for 2 h then concentrated to dryness under vacuum. The residue was redissolved in dichloromethane (4 mL) and added to a mixture of 2-(1H-imidazol-4-yl)-6-(trifluoromethyl)pyridine hydrochloride (0.611 g, 2.136 mmol) and triethylamine (0.94 mL, 6.71 mmol) in dichloromethane (8 mL) and stirred for 2 h. Water (6 mL) was added and the phases were separated and the organic layer dried over anhydrous magnesium sulfate and concentrated. Purification by column chromatography (DCM/MeOH) gave the product as a pale yellow solid in 65% yield.

The following compounds were prepared in a similar manner to that described for Compound 104.

B. (6aS,6bR,8aS,12bR,14bS)-4,4,6a,6b,11,11,14b-heptamethyl-3,13-dioxo-8a-(4-(3-(trifluoromethyl)pyridin-2-yl)-1H-imidazole-1-carbonyl)-3,4,4a,5,6,6a,6b,7,8,8a,9,10,11,12,12a,12b,13,14b-octadecahydropicene-2-carbonitrile (Compound 101)

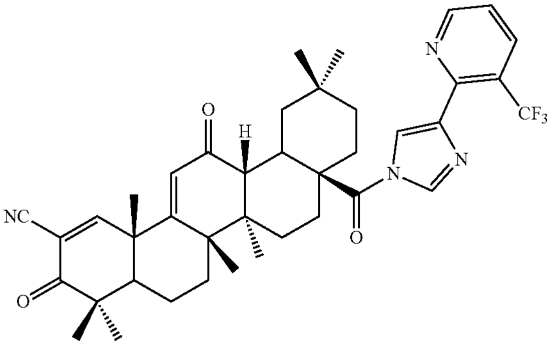

C. (6aS,6bR,8aS,12bR,14bS)-4,4,6a,6b,11,11,14b-heptamethyl-3,13-dioxo-8a-(4-(4-(trifluoromethyl)pyridin-2-yl)-1H-imidazole-1-carbonyl)-3,4,4a,5,6,6a,6b,7,8,8a,9,10,11,12,12a,12b,13,14b-octadecahydropicene-2-carbonitrile (Compound 102)

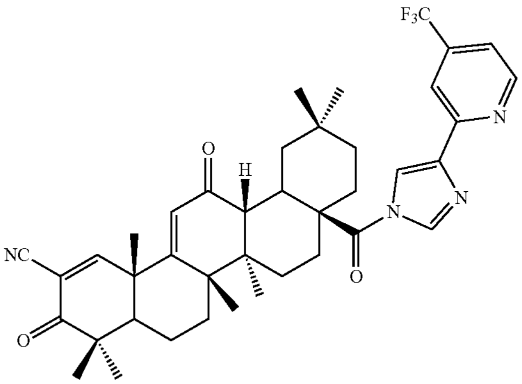

D. (6aS,6bR,8aS,12bR,14bS)-4,4,6a,6b,11,11,14b-heptamethyl-3,13-dioxo-8a-(4-(5-(trifluoromethyl)pyridin-2-yl)-1H-imidazole-1-carbonyl)-3,4,4a,5,6,6a,6b,7,8,8a,9,10,11,12,12a,12b,13,14b-octadecahydropicene-2-carbonitrile (Compound 103)

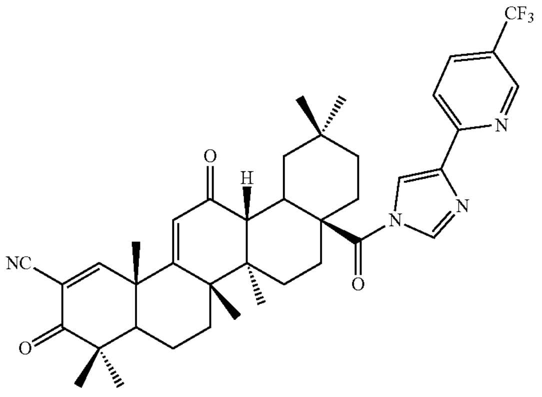

Example 2

A. Preparation of 6-(1-((4aS,6aR,6bS,12aS,14aR)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicene-4a-carbonyl)-1H-imidazol-4-yl)picolinamide (Compound 204)

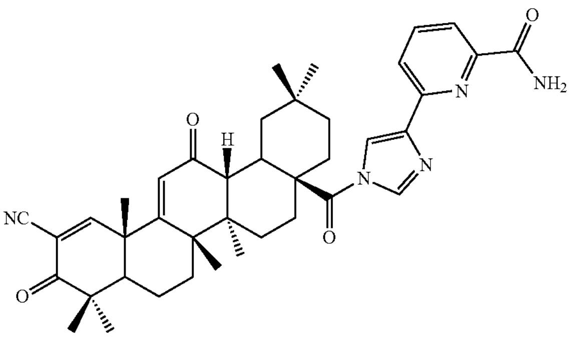

Compound 204 was prepared in a similar manner to Compound 104 except that a bromo-cyanopyridine was used in place of the corresponding bromo-trifluoromethyl pyridine. An additional hydrolysis step was performed prior to trityl deprotection to convert the nitrile to primary amide.

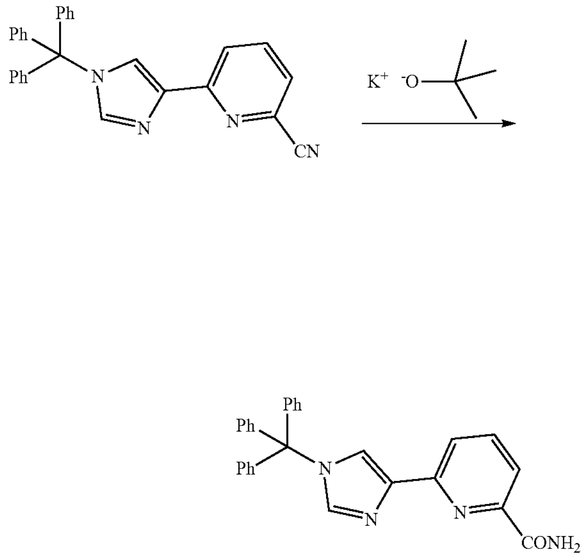

6-(1-trityl-1H-imidazol-4-yl)picolinonitrile (4.46 g, 10.81 mmol) was suspended in t-BuOH (42.37 ml)

Potassium tert-butoxide (3.75 g, 32.4 mmol) was added and the reaction mixture heated to reflux for 2 h. The reaction mixture was cooled to RT and Water (44.6 ml) was added. The reaction mixture was extracted with ethyl acetate, washed with brine and dried over anhydrous magnesium sulfate and concentrated to afford the product in quantitative yield as a yellow solid that was used in the next step without further purification.

The following compounds were prepared in a similar manner to that described for Compound 204.

B. 2-(1-((4aS,6aR,6bS,12aS,14aR)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicene-4a-carbonyl)-1H-imidazol-4-yl)nicotinamide (Compound 201)

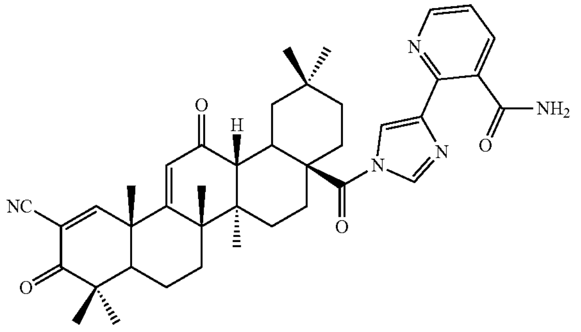

C. 2-(1-((4aS,6aR,6bS,12aS,14aR)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicene-4a-carbonyl)-1H-imidazol-4-yl)isonicotinamide (Compound 202)

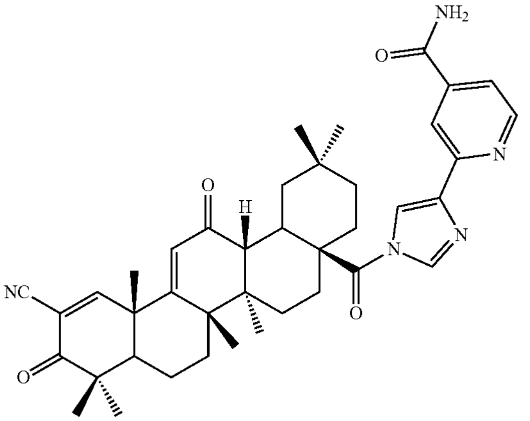

D. 6-(1-((4aS,6aR,6bS,12aS,14aR)-11-cyano-2,2,6a,6b,9,9,12a-heptamethyl-10,14-dioxo-1,2,3,4,4a,5,6,6a,6b,7,8,8a,9,10,12a,14,14a,14b-octadecahydropicene-4a-carbonyl)-1H-imidazol-4-yl)nicotinamide (Compound 203)

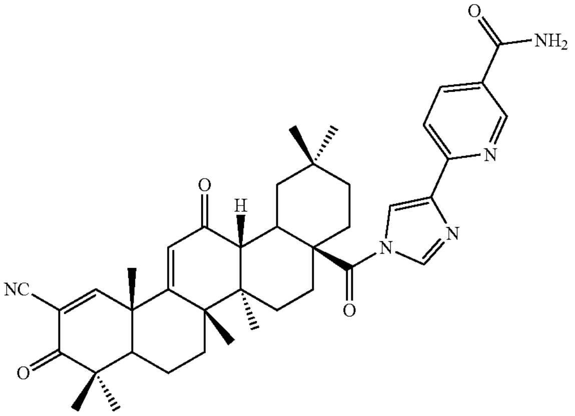

Example 3

A. Preparation of (6aS,6bR,8aS,12bR,14bS)-4,4,6a,6b,11,11,14b-heptamethyl-3,13-dioxo-8a-(4-(5-(trifluoromethyl) pyridin-3-yl)-1H-imidazole-1-carbonyl)-3,4,4a,5,6,6a,6b,7,8,8a,9,10,11,12,12a,12b,13,14b-octadecahydropicene-2-carbonitrile (Compound 303)

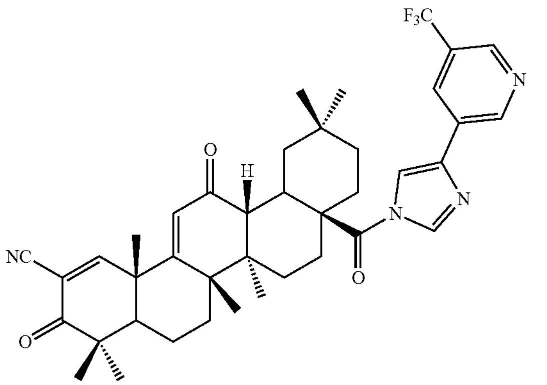

Stille Coupling

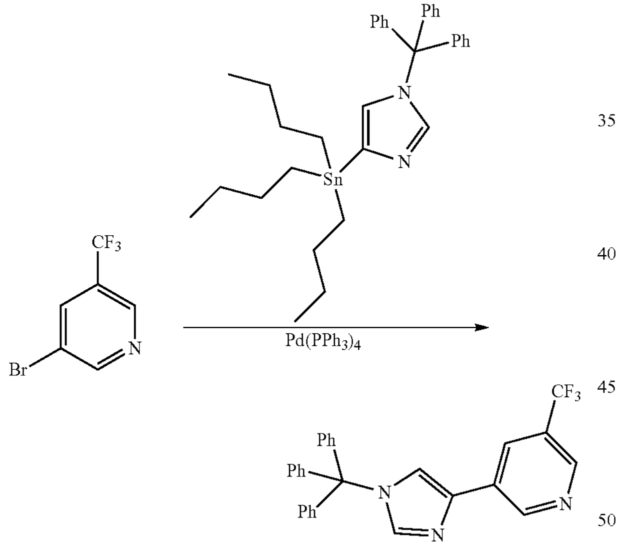

4-(Tributylstannyl)-trityl-1H-imidazole was prepared according to methods known in the art. See Jetter et al., Synthesis 6:829 (1998).

To a stirred solution of 4-(Tributylstannyl)-trityl-1H-imidazole (4.55 g. 7.60 mmol) in toluene (21 mL) was charged 3-bromo-5-(trifluoromethyl)pyridine (1.7 g, 7.52 mmol) and the mixture degassed with nitrogen for 15 minutes. Tetrakis (triphenylphosphine)palladium (0.261 g, 0.226 mmol) was added and the mixture heated to 100° C. and stirred for 18 h. The reaction mixture was cooled to 25° C. and 10% aqueous potassium fluoride (17 mL) solution was added and stirred for 30 minutes. The mixture was filtered through celite and the phases separated. The organic layer was washed twice with water (17 mL) and dried over anhydrous magnesium sulfate and concentrated. Purification by column chromatography (DCM/MeOH 97:3) gave the desired product as a yellow foam in 88% yield.

Trityl Deprotection

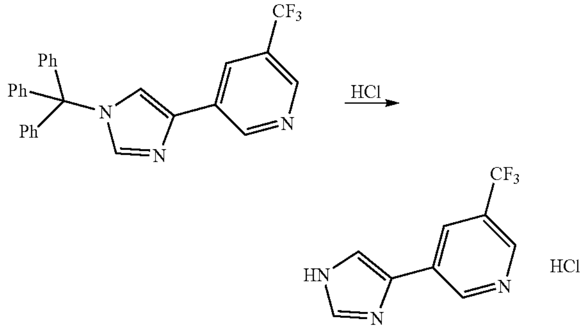

3-(trifluoromethyl)-5-(1-trityl-1H-imidazol-4-yl)pyridine (3.43 g, 7.53 mmol) was dissolved in dioxane (67 mL) and heated to 100° C. HCl in dioxane (5.65 mL, 22.6 mmol, 4M) was added and the mixture heated for 1 h. The mixture was cooled to RT, filtered and washed with dioxane (2×10 mL) and dried under vacuum to give the desired product as a white solid in 85% yield.

Coupling With CDDO

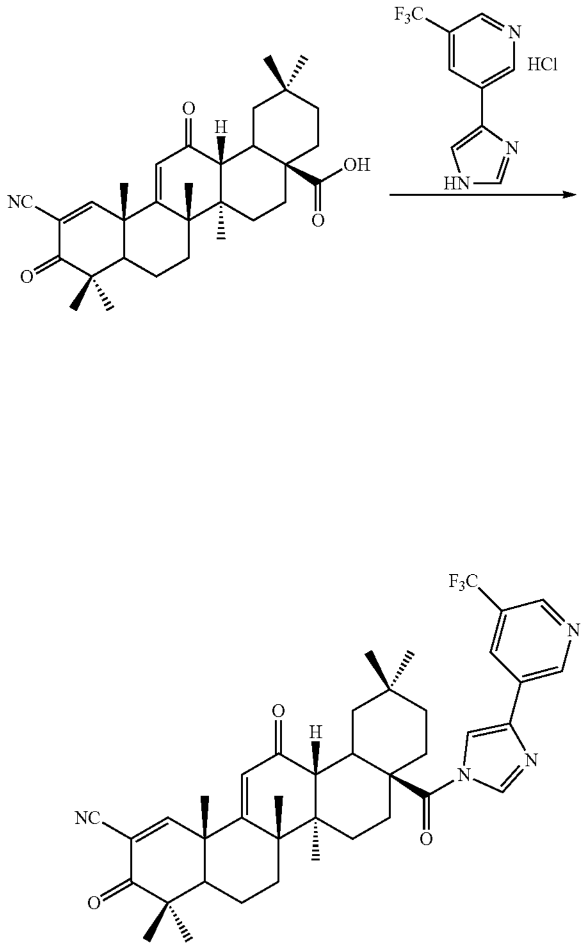

CDDO was obtained from a commercial supplier. To a stirred solution of CDDO (1.6 g, 3.27 mmol) in dichloromethane (16 mL) was added DMF (13 μL, 0.16 mmoL). Oxalyl chloride (0.4 mL, 4.58 mmol) was added over 15 min and the mixture stirred at RT for 2 h then concentrated to dryness under vacuum. The residue was redissolved in dichloromethane (6.4 mL) and added to a mixture of 3-(1H-imidazol-4-yl)-5-(trifluoromethyl)pyridine dihydrochloride (0.984 g, 3.44 mmol) and triethylamine (1.56 mL, 10.8 mmol) in dichloromethane (13 mL) and stirred for 2 h. Water (10 mL) was added and the phases were separated and the organic layer dried over anhydrous magnesium sulfate and concentrated. Purification by column chromatography (DCM/MeOH) gave the product as a pale yellow solid in 58% yield.

The following compounds were prepared in a similar manner to that described for Compound 303.

B. (6aS,6bR,8aS,12bR,14bS)-4,4,6a,6b,11,11,14b-heptamethyl-3,13-dioxo-8a-(4-(2-(trifluoromethyl)pyridin-3-yl)-1H-imidazole-1-carbonyl)-3,4,4a,5,6,6a,6b,7,8,8a,9,10,11,12,12a,12b,13,14b-octadecahydropicene-2-carbonitrile (Compound 301)

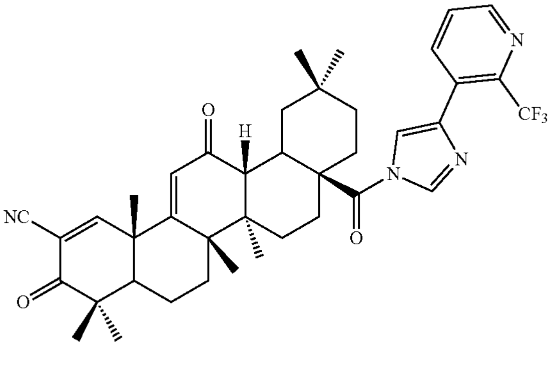

C. (6aS,6bR,8aS,12bR,14bS)-4,4,6a,6b,11,11,14b-heptamethyl-3,13-dioxo-8a-(4-(4-(trifluoromethyl)pyridin-3-yl)-1H-imidazole-1-carbonyl)-3,4,4a,5,6,6a,6b,7,8,8a,9,10,11,12,12a,12b,13,14b-octadecahydropicene-2-carbonitrile (Compound 302)

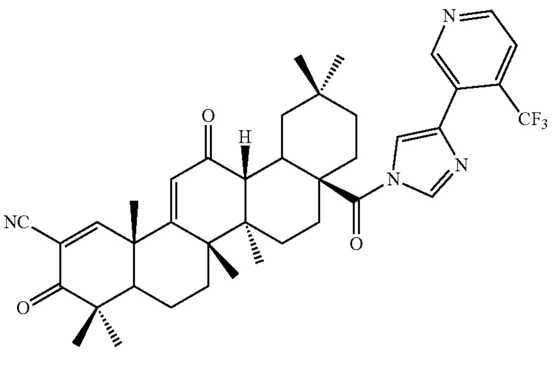

D. (6aS,6bR,8aS,12bR,14bS)-4,4,6a,6b,11,11,14b-heptamethyl-3,13-dioxo-8a-(4-(6-(trifluoromethyl)pyridin-3-yl)-1H-imidazole-1-carbonyl)-3,4,4a,5,6,6a,6b,7,8,8a,9,10,11,12,12a,12b,13,14b-octadecahydropicene-2-carbonitrile (Compound 304)

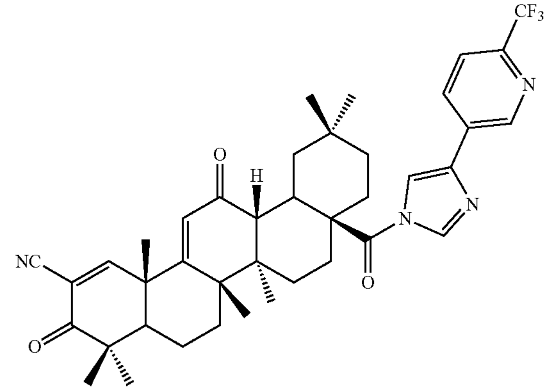

Example 4

Compounds 401-404 are prepared in a similar manner as Example 3 except that a bromo-cyanopyridine is used in place of the corresponding bromo-trifluoromethyl pyridine. An additional hydrolysis step is performed prior to trityl deprotection to convert the nitrile to primary amide.

A. CDDO-3P-Im-2-carboxamide (Compound 401).

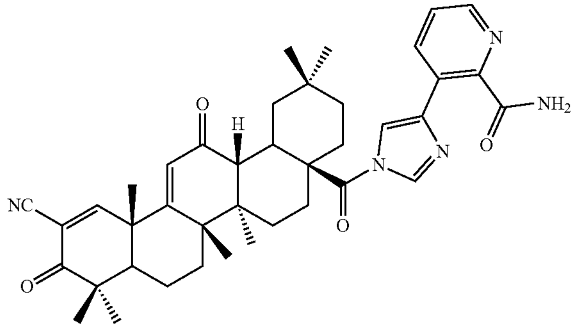

B. CDDO-3P-Im-4-carboxamide (Compound 402).

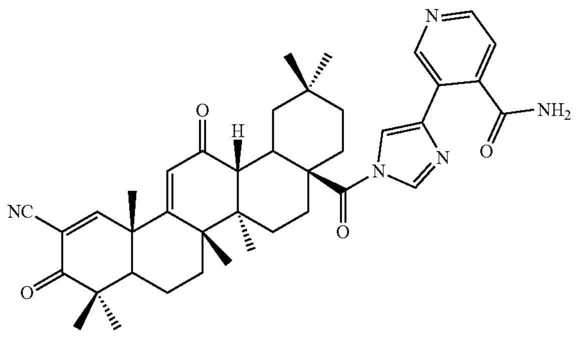

C. CDDO-3P-Im-5-carboxamide (Compound 403).

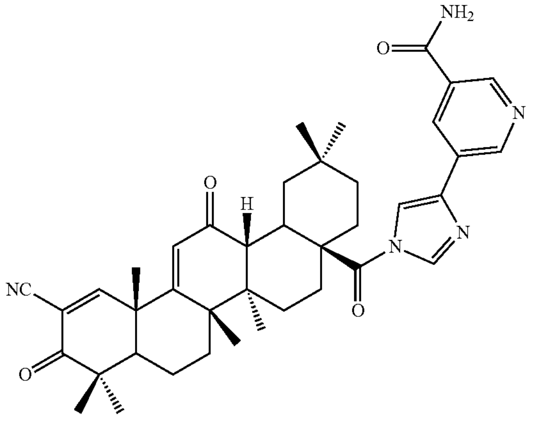

D. CDDO-3P-Im-6-carboxamide (Compound 404).

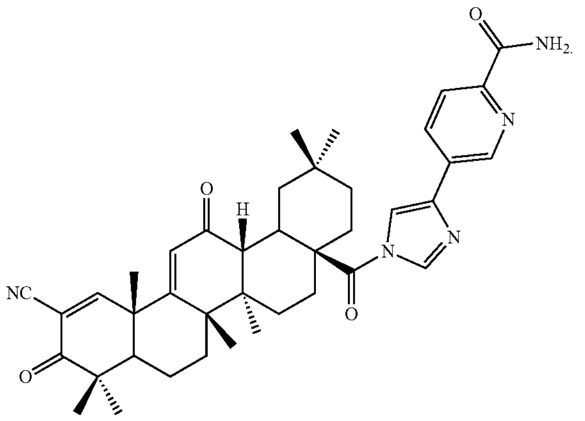

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicant reserves the right to challenge the accuracy and pertinence of the cited references.

What is claimed is:

1. A compound or an N-oxide thereof or a pharmaceutically acceptable salt thereof, wherein the compound has a structure corresponding to Formula (I) or Formula (III):

(I)

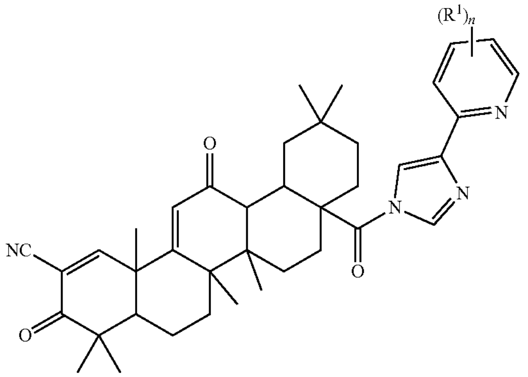

(III)

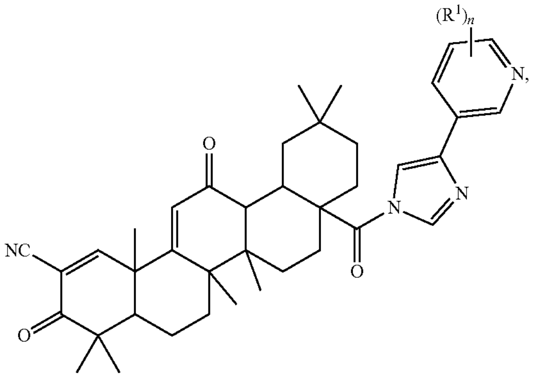

wherein n is an integer selected from 1 to 4 and $R^1$ is halogen, optionally substituted carboxamide, or optionally substituted $C_{1-6}$-haloalkyl.

2. The compound, N-oxide, or salt of claim 1, wherein n is 1.

3. The compound, N-oxide, or salt of claim 1, wherein $R^1$ is $C_{1-6}$-haloalkyl.

4. The compound, N-oxide, or salt of claim 1, wherein $R^1$ is $C_{1-6}$-fluoroalkyl.

5. The compound, N-oxide, or salt of claim 1, wherein $R^1$ is —$CF_3$.

6. The compound, N-oxide, or salt of claim 1, wherein $R^1$ is an optionally substituted carboxamide.

7. The compound, N-oxide, or salt of claim 1, wherein $R^1$ is —$C(O)NH_2$.

8. A compound or an N-oxide thereof or a pharmaceutically acceptable salt thereof, wherein the compound has a structure corresponding to Formula (II) or Formula (IV):

(II)

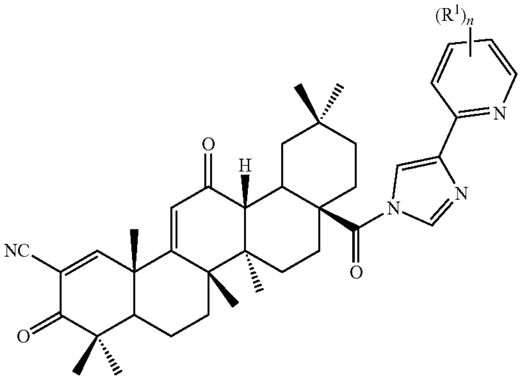

-continued (IV)

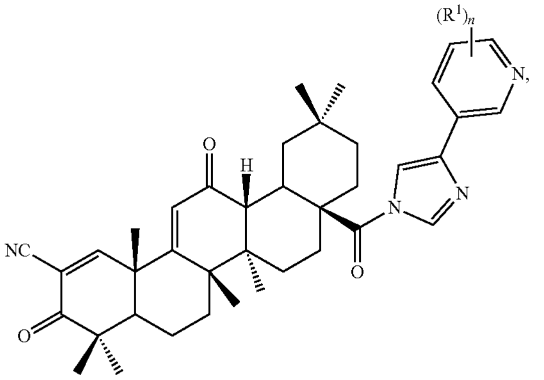

wherein n is an integer selected from 1 to 4 and $R^1$ is halogen, optionally substituted carboxamide, or optionally substituted $C_{1-6}$-haloalkyl.

9. The compound, N-oxide, or salt of claim 8, wherein n is 1.

10. The compound, N-oxide, or salt of claim 8, wherein $R^1$ is $C_{1-6}$-haloalkyl.

11. The compound, N-oxide, or salt of claim 8, wherein $R^1$ is $C_{1-6}$-fluoroalkyl.

12. The compound, N-oxide, or salt of claim 8, wherein $R^1$ is —$CF_3$.

13. The compound, N-oxide, or salt of claim 8, wherein $R^1$ is an optionally substituted carboxamide.

14. The compound, N-oxide, or salt of claim 8, wherein $R^1$ is —$C(O)NH_2$.

15. The compound, N-oxide, or salt of claim 8, wherein the compound has a structure corresponding to:

| Compound | Structure |
|---|---|
| 101 | 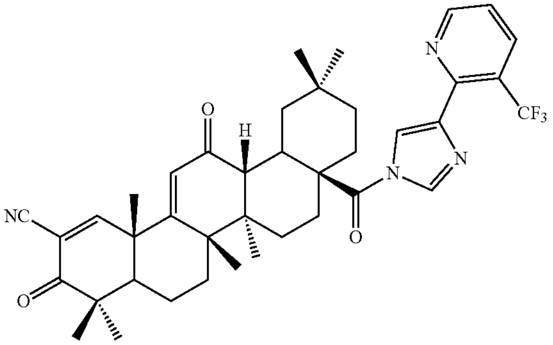 |
| 102 | 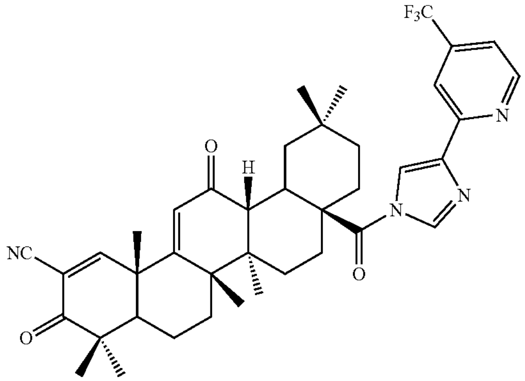 |

-continued
| Compound | Structure |
| --- | --- |
| 103 | 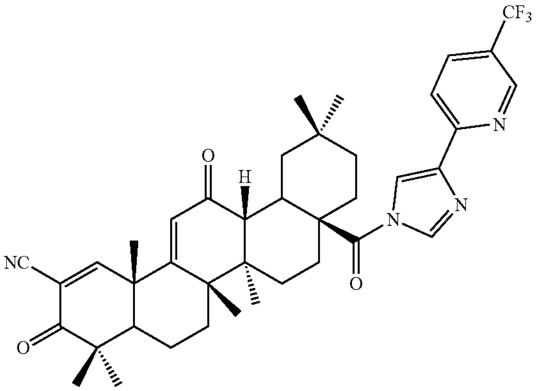 |
| 104 | 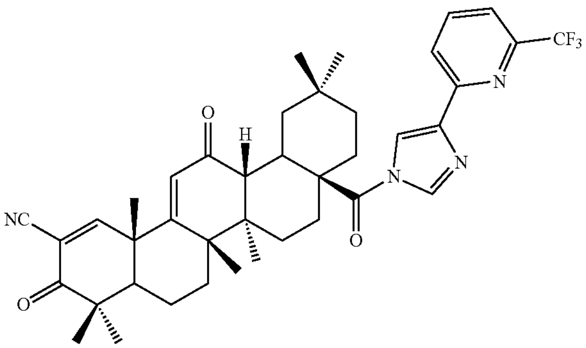 |
| 201 | 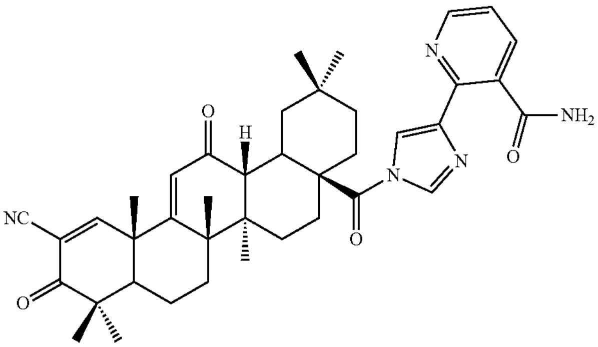 |
| 202 | 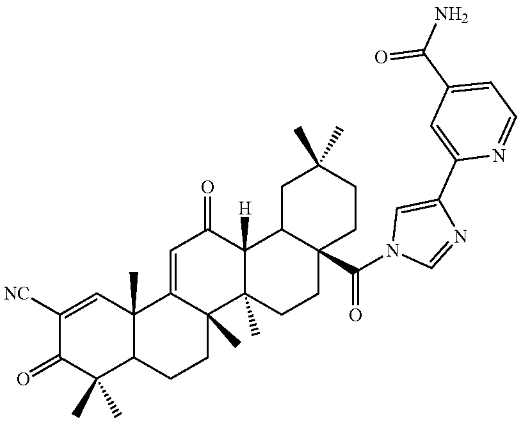 |

-continued
| Compound | Structure |
|---|---|
| 203 | 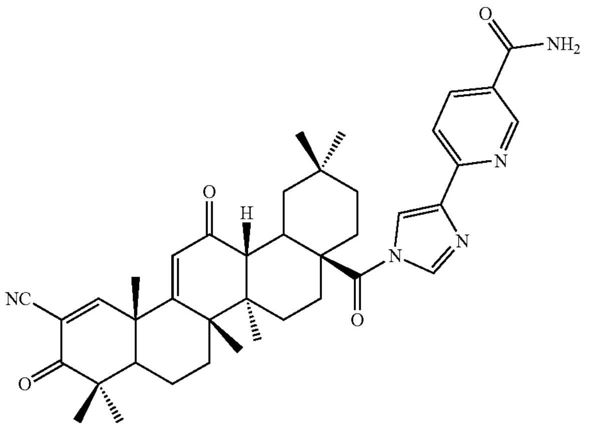 |
| 204 | 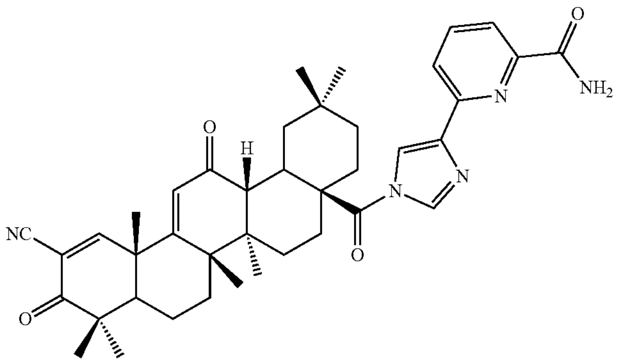 |
| 301 | 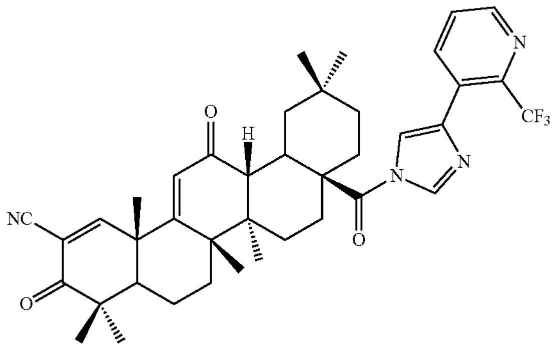 |
| 302 | 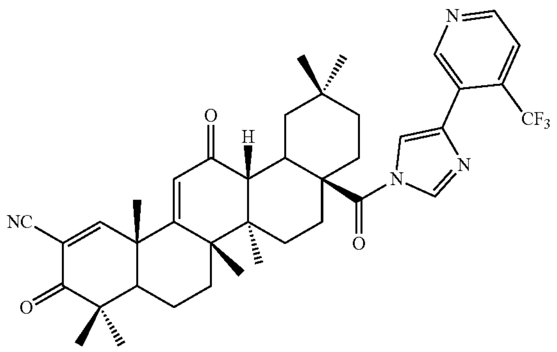 |

-continued
| Compound | Structure |
| --- | --- |
| 303 | 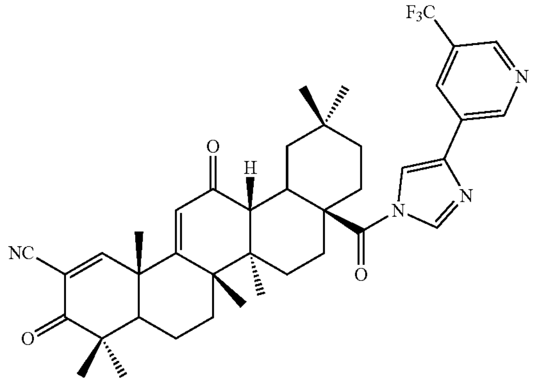 |
| 304 | 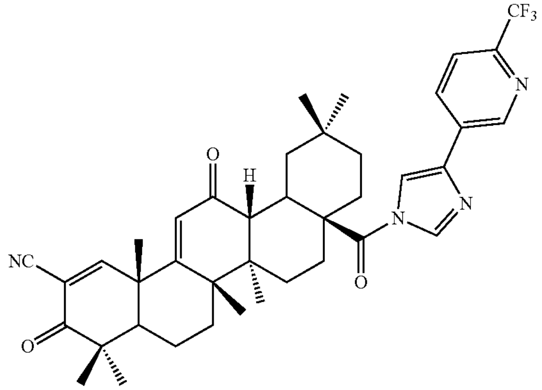 |
| 401 | 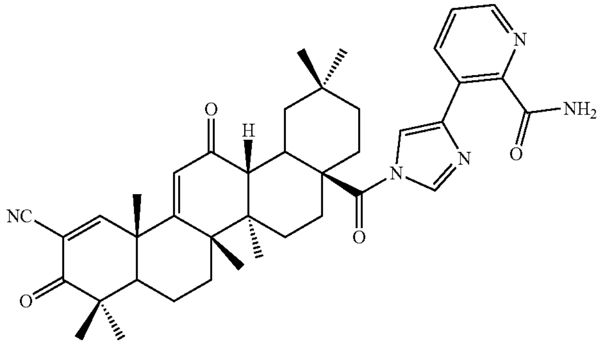 |
| 402 | 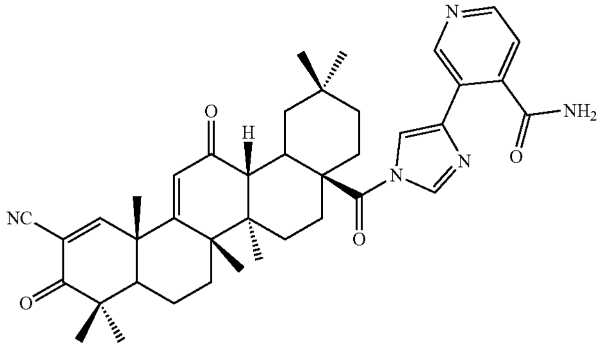 |

-continued

| Compound | Structure |
| --- | --- |
| 403 | 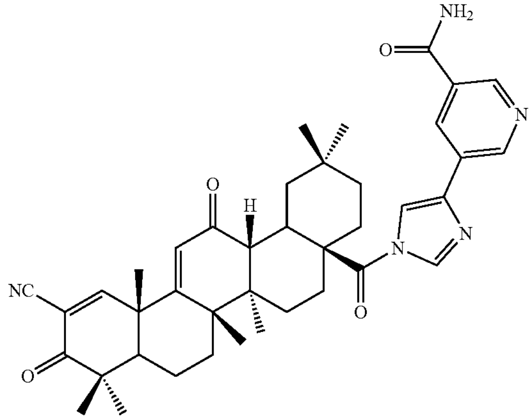 |
| 404 | 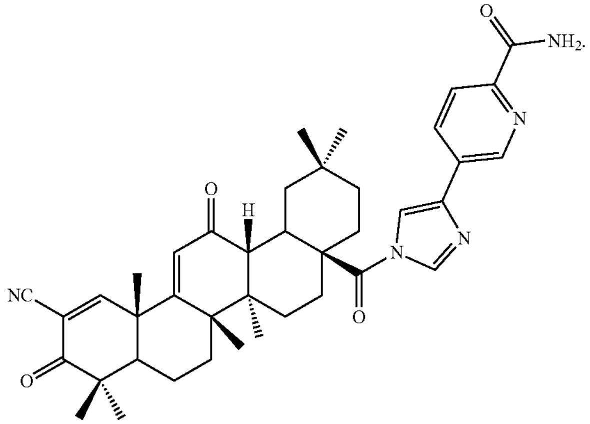 |

16. A method for inhibiting Nrf2 activity in a patient in need thereof, the method comprising: administering to the patient the compound, or N-oxide, or salt of claim 1.

17. A method for treating brain cancer in a patient in need thereof, the method comprising: administering to the patient an effective amount the compound, or N-oxide, or salt of claim 1.

18. The method of claim 17, wherein the brain cancer is a glioma.

19. A pharmaceutical composition comprising (i) the compound, or N-oxide, or salt of claim 1 and (ii) a pharmaceutically acceptable excipient.

20. The method of claim 16, wherein the patient has a neurodegenerative disease.

21. The method of claim 16, wherein the patient has brain cancer.

22. The method of claim 16, wherein the patient has a glioma.

* * * * *